(12) United States Patent
Safadi

(10) Patent No.: US 11,098,116 B2
(45) Date of Patent: Aug. 24, 2021

(54) INHIBITORS OF NEUROLIGIN 4-NEUREXIN 1-BETA PROTEIN-PROTEIN INTERACTION FOR TREATMENT OF LIVER DISORDERS

(71) Applicant: HADASIT MEDICAL RESEARCH SERVICES AND DEVELOPMENT LTD., Jerusalem (IL)

(72) Inventor: Rifaat Safadi, Nazareth Elit (IL)

(73) Assignee: HADASIT MEDICAL RESEARCH SERVICES AND DEVELOPMENT LTD., Jerusalem (IL)

(*) Notice: Subject to any disclaimer, the term of this patent is extended or adjusted under 35 U.S.C. 154(b) by 0 days.

(21) Appl. No.: 16/407,848

(22) Filed: May 9, 2019

(65) Prior Publication Data

US 2019/0389948 A1 Dec. 26, 2019

Related U.S. Application Data

(62) Division of application No. 15/562,602, filed as application No. PCT/IL2016/050351 on Mar. 31, 2016, now abandoned.

(60) Provisional application No. 62/141,299, filed on Apr. 1, 2015.

(51) Int. Cl.
| | |
|---|---|
| *C07K 16/28* | (2006.01) |
| *A61K 38/16* | (2006.01) |
| *A61K 38/17* | (2006.01) |
| *A61P 1/16* | (2006.01) |
| *A61K 39/00* | (2006.01) |

(52) U.S. Cl.
CPC .............. *C07K 16/28* (2013.01); *A61K 38/16* (2013.01); *A61K 38/177* (2013.01); *A61K 38/1709* (2013.01); *A61P 1/16* (2018.01); *A61K 2039/505* (2013.01); *C07K 2317/34* (2013.01); *C07K 2317/52* (2013.01); *C07K 2317/76* (2013.01); *C07K 2319/30* (2013.01)

(58) Field of Classification Search
CPC ................ C07K 16/28; C07K 2317/34; C07K 2317/52; C07K 2317/76; C07K 2319/30; A61K 38/16; A61K 38/1709; A61K 38/177; A61K 2039/505; A61P 1/16
See application file for complete search history.

(56) References Cited

U.S. PATENT DOCUMENTS

| | | |
|---|---|---|
| 4,816,567 A | 3/1989 | Cabilly |
| 5,641,870 A | 6/1997 | Rinderknecht |
| 5,910,573 A | 6/1999 | Plueckthun |
| 7,579,392 B2 | 8/2009 | Gan |
| 8,256,790 B2 | 9/2012 | Fortner |
| 8,817,788 B2 | 8/2014 | Kakumaru |
| 8,999,554 B2 | 4/2015 | Lee |
| 2014/0051597 A1 | 2/2014 | Sarwal |

FOREIGN PATENT DOCUMENTS

| | | |
|---|---|---|
| EP | 404097 A2 | 12/1990 |
| WO | 9311161 A1 | 6/1993 |
| WO | 9315210 A1 | 8/1993 |
| WO | 9613583 A2 | 5/1996 |
| WO | 9637621 A2 | 11/1996 |
| WO | 2009033743 A1 | 3/2009 |

OTHER PUBLICATIONS

Gunter et al. "CIRRHOSIS: advanced liver disease". Retrieved on Jun. 21, 2020 from http://www.natap.org/2002/Oct/103002_2.htm, published Feb. 1, 2002.*
Abu-Tair et al., (2013) 1102 Neuroligin-4 receptor silencing increased human natural killer activity and decreased hepatic stellate cells activation. Journal of Hepatology, 58, S450.
Amer et al., (2013) 1244 NLGn4 and NMDA receptors mediate NK cell activity via mTOR pathway in NAFLD. Journal of Hepatology 58, Supplement 1, p. S504.
Amer et al., (2014) O155 Homozygous NLG4 (KO) mice showed a decreased inflammatory and fibrotic profile and is associated with NK cells increased killing activity. Journal of Hepatology, 60(1), S64.
Amer et al., (2015) P0502: Recombinant neuroligin 4 (NLG4) activates NK cells and attenuates fibrogenesis in nonalcoholic fatty liver disease. Journal of Hepatology, 62, S503.
Bird et al., (1988) Single-chain antigen-binding proteins. Science, 242(4877), 423-427.
Brisson et al., (1984) Expression of a bacterial gene in plants by using a viral vector. Nature, 310(5977), 511-514.
Broglie et al., (1984) Light-regulated expression of a pea ribulose-1, 5-bisphosphate carboxylase small subunit gene in transformed plant cells. Science, 224, 838-844.
Chothia & Lesk, (1987) Canonical structures for the hypervariable regions of immunoglobulins. Journal of molecular biology, 196(4), 901-917.
Clackson & Hoogenboom, (1991) Making antibody fragments using phage display libraries. Nature, 352(6336), 324-628.
Coruzzi et al., (1984) Tissue-specific and light-regulated expression of a pea nuclear gene encoding the small subunit of ribulose-1, 5-bisphosphate carboxylase. The EMBO journal, 3(8), 1671-1679.
Gurley et al., (1986) Upstream sequences required for efficient expression of a soybean heat shock gene. Molecular and cellular biology, 6(2), 559-565.
Holliger et al., (1993) "Diabodies": small bivalent and bispecific antibody fragments. Proceedings of the National Academy of Sciences, 90(14), 6444-6448.
Hoon et al., (2011) Neuroligin-4 is localized to glycinergic postsynapses and regulates inhibition in the retina. Proc Natl Acad Sci U S A, 108(7), 3053-3058.

(Continued)

*Primary Examiner* — Gregory S Emch
(74) *Attorney, Agent, or Firm* — J.A. Lindeman & Co., PLLC

(57) ABSTRACT

Method for treating, attenuating and/or preventing progression of a liver disorder in a subject, the method including administering a therapeutically effective amount of an agent capable of interfering with, inhibiting and/or preventing neuroligin 4 (NLGn4)-Neurexin 1-beta (Nrx1b) protein-protein interaction; and compositions including the agent.

13 Claims, 7 Drawing Sheets

Specification includes a Sequence Listing.

(56) References Cited

OTHER PUBLICATIONS

Huston et al., (1988) Protein engineering of antibody binding sites: recovery of specific activity in an anti-digoxin single-chain Fv analogue produced in *Escherichia coli*. Proceedings of the National Academy of Sciences, 85(16), 5879-5883.
Jones et al., (1986) Replacing the complementarity-determining regions in a human antibody with those from a mouse. Nature, 321(6069), 522-525.
Köhler & Milstein, (1975) Continuous cultures of fused cells secreting antibody of predefined specificity. Nature, 256(5517), 495-497.
Kozbor & Roder, (1983) The production of monoclonal antibodies from human lymphocytes. Immunology Today, 4(3), 72-79.
Leone et al., (2010) Structural insights into the exquisite selectivity of neurexinlneuroligin synaptic interactions. The EMBO journal, 29(14), 2461-2471.
Marks et al., (1991) By-passing immunization: human antibodies from V-gene libraries displayed on phage. Journal of molecular biology, 222(3), 581-597.
Melhem et al., (2006) Anti-fibrotic activity of NK cells in experimental liver injury through killing of activated HSC. Journal of hepatology, 45(1), 60-71.
Riechmann et al., (1988) Reshaping human antibodies for therapy. Nature, 332(6162), 323-327.
Seki et al., (2011) Antitumor Immunity Produced by the Liver Kupffer Cells, NK Cells, NKT Cells, and CD8. Journal of Immunology Research, 1-9.
Sims et al., (1993) A humanized CD18 antibody can block function without cell destruction. The Journal of Immunology, 151(4), 2296-2308.
Suckow et al., (2008) Expression of neurexin, neuroligin, and their cytoplasmic binding partners in the pancreatic beta-cells and the involvement of neuroligin in insulin secretion. Endocrinology, 149(12), 6006-6017.
Takahashi et al., (2015) Current pharmacological therapies for nonalcoholic fatty liver disease/nonalcoholic steatohepatitis. World J Gastroenterol, 21(13), 3777-3785.
Takamatsu et al., (1987) Expression of bacterial chloramphenicol acetyltransferase gene in tobacco plants mediated by TMV-RNA. The EMBO journal, 6(2), 307-311.
Verhoeyen et al., (1988) Reshaping human antibodies: grafting an antilysozyme activity. Science, 239(4847), 1534-1536.
Ward et al., (1989) Binding activities of a repertoire of single immunoglobulin variable domains secreted from *Escherichia coli*. Nature, 341(6242), 544-546.
Zapata et al., (1995) Engineering linear F (ab') 2 fragments for efficient production in *Escherichia coli* and enhanced antiproliferative activity. Protein Engineering, Design and Selection, 8(10), 1057-1062.
Zhang, et al (2016) Liver fibrosis and hepatic stellate cells: Etiology, pathological hallmarks and therapeutic targets, World J of Gastroenteroloogy, 22(48):10512-10522.
Adinolfi et al (2016) NAFLS and NASH in HCV Infection: Prevalence and Significance in Hepatic and Extrahepatic Manifestations, Int. J. Mol. Sci. 17(803.
Enomoto et al (2015) Liver fibrosis markers of nonalcoholic steatohepatitis, World J Gastroenterology, 21(24): 7427-7435.
Yu et al (2015) Serum Interleukin (IL)-9 and IL-10, but not T-Helper 9 (Th-9) Cells, are Associated With Survival of Patients With Acute-on-Chronic Hepatitis B Liver Failure, Medicine 95(16).
Ramos-Lopez et al (2015) Genetic, metabolic and environmental factors involved in the development of liver cirrhosis in Mexico, World J Gastroenterology 21(41): 11552-11566.
Tang et al (2016) Systemic Manifestations of Hepatitis C Infection, Infectious Agents and Cancer, 11:29.
Wang et al (2016) Adipose tissue-liver axis in alcoholic liver disease, World J Gastrointestinal Pathophysiology, 7(1) 17-26.

\* cited by examiner

INHIBITORS OF NEUROLIGIN 4-NEUREXIN 1-BETA PROTEIN-PROTEIN INTERACTION FOR TREATMENT OF LIVER DISORDERS

FIELD OF THE INVENTION

The present invention relates to antibodies and recombinant proteins capable of interfering with, inhibiting and/or preventing neuroligin-4 (NLGn4)-neurexin 1β (Nrx1b) protein-protein interaction, and to the use thereof for the treatment and/or attenuation of liver disorders.

SEQUENCE LISTING

The Sequence Listing submitted herewith as an ASCII text file (2019-08-21_Sequence_Listing.txt, created on Aug. 15, 2019, 32453 bytes) via EFS-Web is hereby incorporated reference.

BACKGROUND OF THE INVENTION

The normal liver is composed of hepatocytes and non-parenchymal cells, which include Kupffer cells, sinusoidal endothelial cells, and myofibroblasts known as Hepatic Stellate Cells (HSCs). HSCs are considered involved in the pathogenesis of liver fibrosis from any etiology, including NASH-related hepatic fibrosis and hepatocellular carcinoma. In normal liver, HSCs are in a quiescent state and serve to store retinoids (vitamin A). Quiescent stellate cells represent 5-8% of the total number of liver cells. When the liver is damaged, HSCs change into an activated state characterized by contractions, loss of lipid droplets, enhanced proliferation, cell migration and cellular adhesion. HSCs are also unequivocally the main cells involved in the production of excessive ECM seen in liver fibrosis. Since activated HSCs themselves secrete inflammatory chemokines, a vicious cycle is formed, whereby fibrogenic and inflammatory cells stimulate each other and perpetuate a process of liver damage and repair.

Natural killer (NK) cells are a key component of the innate immune system, and play a critical role in the early stages of the immune response against tumor cells, as well as those infected by viral and microbial pathogens.

In humans, two NK-cell subsets have been characterized according to the cell-surface density of CD56 and expression of CD16. $CD56^{dim}CD16^{bright}$ NK cells (hereinafter $CD56^{dim}$) compose approximately 90% of circulating NK cells; $CD56^{bright}CD16^{dim}$ NK cells (hereinafter $CD56^{bright}$) constitute approximately 10%. $CD56^{bright}$ NK cells proliferate and produce interferon in response to stimulation with interleukin-12 (IL-12), whereas $CD56^{dim}$ NK cells are more cytolytic and produce significant amounts of cytokine when their activating receptors are engaged.

In a paper on which the inventor is a principle investigator, it was found that, as opposed to CD8 immune cells, NK cells have anti-fibrotic activity through HSC killing (Melhem et al., J. Hepatology; 2006; 45: 60-71). It has also been reported that the function of NK cells decreases when the liver disease progresses into cirrhosis, suggesting that attenuating NK function is a prerequisite for the progression of the disease (Seki et al.; Clin Dev Immunol.; 2011; Article ID 868345).

Human neuroligin-4 (NLG4, NLGn4, NLGn4X) is a family member of neuronal cell surface proteins called the Neuroligins. FIG. 1 illustrates the neuroligins and their interactions. Members of this family are membrane-anchored proteins acting as ligands for beta-neurexins and are thought to be involved in the formation and remodeling of central nervous system synapses. The encoded protein interacts with discs, large (Drosophila) homolog 4 (DLG4). Mutations in this gene have been associated with autism and Asperger syndrome. High levels of NLGn4 has been reported heart tissue and lower levels in liver, skeletal muscle and pancreas.

Neurexin (NRXN) is a presynaptic protein that helps to glue together neurons at the synapse. Neurexins are located mostly on the presynaptic membrane and contain a single transmembrane domain. The extracellular domain interacts with proteins in the synaptic cleft, most notably neuroligin, while the intracellular cytoplasmic portion interacts with proteins associated with exocytosis.

Non-alcoholic fatty-liver disease (NAFLD) is one of the most prevalent liver diseases in western countries. The full pathophysiology of NAFLD is still unknown. Both obesity and insulin resistance are considered to play a strong role in the disease process. Indeed, the rising rates of obesity and diabetes mellitus correlate with the increasing incidence of NAFLD, which is the hepatic and early manifestation of metabolic syndrome. Estimates suggest that about 20% to 30% of adults in developed countries have excess fat accumulation in the liver, 50% among people with diabetes, and about 80% in the obese and morbidly obese individuals.

Non-alcoholic steatohepatitis (NASH) is the most severe form of NAFLD, and can progress to more severe forms of liver disease, including fibrosis, cirrhosis, and hepatocellular carcinoma.

The disease begins with the aberrant accumulation of triglycerides in the liver, resulting in simple steatosis; most patients who develop steatosis are stable and further disease does not develop. However, some individuals progress to NASH, the severe form of NAFLD. In NASH, up to 20% of patients' progress into cirrhosis. The clinical implications of NAFLD are derived mostly from its potential to progress to cirrhosis and liver failure.

There is an unmet medical need for compositions and methods for treating NAFLD and preventing the progression to cirrhosis and hepatocellular carcinoma. Nowhere in the art has it been suggested that treating, attenuating and/or preventing progression of liver disorders can be achieved by administering an agent capable of interfering with, inhibiting and/or preventing NLGn4-Nrx1b protein-protein interaction.

SUMMARY OF THE INVENTION

The present invention stems, in part, from the surprising finding that liver disorders can be treated and/or attenuated by administering to a subject in need thereof an agent capable of interfering, inhibiting and/or preventing NLGn4-Nrx1b protein-protein interaction. The agent may be an anti-NLGn4 antibody, an anti-Nrx1b antibody, recombinant NLGn4, recombinant Nrx1b or any fragment, analog or derivative thereof capable of interfering, inhibiting and/or preventing the NLGn4-Nrx1b interaction.

According to some embodiments, the invention provides a method of treating, attenuating and/or preventing progression of a liver disorder in a subject, the method comprising administering to the subject in need thereof a therapeutically effective amount of an agent capable of interfering, inhibiting and/or preventing with neuroligin 4 (NLGn4)-Neurexin 1β (Nrx1b) protein interaction; thereby treating, attenuating and/or preventing progression of the liver disorder.

According to some embodiments, the invention provides a composition for use in the treatment, attenuation and/or prevention of progression of a liver disorder, the composition comprising a therapeutically effective amount of an agent capable of interfering, inhibiting and/or preventing with neuroligin 4 (NLGn4)-Neurexin 1β (Nrx1b) protein interaction. According to some embodiments, the composition is suitable for administration to a subject suffering from a liver disorder. According to some embodiments, the composition is suitable for administration to an immune cell population of the subject.

According to some embodiments, the agent comprises recombinant NLGn4. According to some embodiments, the recombinant NLGn4 is soluble (rsNLGn4); wherein the rsNLGn4 comprises the extracellular domain of NLGn4 as set forth in SEQ ID NO: 7 or a fragment, derivative or analog thereof. According to some embodiments, the rsNLGn4 consists essentially of SEQ ID NO: 7 or a fragment, derivative or analog thereof. According to some embodiments, the recombinant NLGn4 comprises Gln42-Ser676 of NP_065793. According to some embodiments, the recombinant NLGn4 consists essentially of Gln42-Ser676 of NP_065793.

According to some embodiments, the rsNLGn4 competes with endogenous NLGn4 for binding to Nrx1b.

According to some embodiments, the rsNLGn4 is devoid of the intracellular domain and/or the transmembrane domain of NLGn4.

According to some embodiments, the agent comprises a fusion protein comprising rsNLGn4 and an immunoglobulin molecule. According to some embodiments, the agent comprises a fusion protein comprising rsNLGn4 and an Fc domain of an immunoglobulin molecule, also referred to herein as rsNGLn4-Fc fusion protein and rsNLGn4-Fc chimera. According to some embodiments, the Fc domain may include part or the entire CH1 domain, CH2 domain, CH3 domain and hinge region of IgG1, IgG2, IgG3 and IgG4. According to some embodiments, the Fc domain may be devoid of the CH1 domain. According to some embodiments, the Fc domain comprises Pro100-Lys330 of Human IgG1. According to some embodiments, the Fc domain consists essentially of Pro100-Lys330 of Human IgG1. According to some embodiments, the Fc domain may be linked to rsNLGn4 through a linker. According to some embodiments, the linker may include the amino acid sequence set forth in SEQ ID NO: 13 (IEGRMD).

According to some embodiments, the agent is a chimeric protein formed from NLGn4 polypeptides or fragments fused with a second polypeptide to form a soluble NLGn4. According to some embodiments, the agent comprises a DNA sequences, which combine two partial DNA sequences, one sequence encoding soluble fragments of NLGn4 (i.e. the DNA sequence encoding the extracellular domain of NLGn4) and the other partial sequence encoding all domains except the first domain of the constant region of the heavy chain of human immunoglobulin IgG, IgA, IgM, or IgE. These DNA sequences may subsequently be expressed in target cells using expression vectors as known in the art, thereby obtaining endogenous expression of recombinant proteins having the extracellular domain of NLGn4 joined to the Fc fragment of an immunoglobulin molecule.

According to some embodiments, the agent comprises recombinant Nrx1b. According to some embodiments, the recombinant Nrx1b is soluble (rsNrx1b); wherein the rsNrx1b comprises the extracellular domain of Nrx1b as set forth in SEQ ID NO: 10 or a fragment, derivative or analog thereof. According to some embodiments, the recombinant Nrx1b comprises Ala51-Ser363 of NP_620072. According to some embodiments, the recombinant Nrx1b consists essentially of Ala51-Ser363 of NP_620072. According to some embodiments, the rsNrx1b consists essentially of SEQ ID NO: 10 or a fragment, derivative or analog thereof.

According to some embodiments, the rsNrx1b competes with endogenous Nrx1b for binding to NLGn4.

According to some embodiments, the rsNrx1b is devoid of the intracellular domain and/or the transmembrane domain of Nrx1b.

According to some embodiments, NLGn4 is encoded by the sequence set forth in SEQ ID NO: 1.

According to some embodiments, the agent comprises a fusion protein comprising rsNrx1b and an immunoglobulin molecule. According to some embodiments, the agent comprises a fusion protein comprising rsNrx1b and an Fc domain of an immunoglobulin molecule, also referred to herein as rsNrx1b-Fc fusion protein and rsNrx1b-Fc chimera. According to some embodiments, the Fc domain may include part or all of the CH1 domain, the CH2 domain, the CH3 domain and hinge region of IgG1, IgG2, IgG3 and IgG4. According to some embodiments, the Fc domain may be devoid of the CH1 domain. According to some embodiments, the Fc domain may include all domains of the Fc domain apart from CH1. According to some embodiments, the Fc domain comprises Pro100-Lys330 of Human IgG1. According to some embodiments, the Fc domain consists essentially of Pro100-Lys330 of Human IgG1. According to some embodiments, the Fc domain may be linked to rsNrx1b through a linker. According to some embodiments, the linker may have the amino acid sequence set forth in SEQ ID NO: 13 (IEGRMD).

According to some embodiments, the agent is a chimeric protein formed from Nrx1b polypeptides or fragments fused with a second polypeptide to form a soluble Nrx1. According to some embodiments, the agent comprises a DNA sequences, which combine two partial DNA sequences, one sequence encoding soluble fragments of Nrx1b (i.e. the DNA sequence encoding the extracellular domain of Nrx1b) and the other partial sequence encoding all domains except the first domain of the constant region of the heavy chain of human immunoglobulin IgG, IgA, IgM, or IgE. These DNA sequences may subsequently be expressed in target cells using expression vectors as known in the art, thereby obtaining endogenous expression of recombinant proteins having the extracellular domain of Nrx1b joined to the Fc fragment of an immunoglobulin molecule.

According to some embodiments, Nrx1b is encoded by the sequence set forth in SEQ ID NO: 6.

According to some embodiments, the agent is an antibody to human NLGn4 and/or its receptor Nrx1b.

According to some embodiments, the antibody is a monoclonal antibody, according to additional embodiments the antibody is a humanized monoclonal antibody. According to some embodiments, the humanized monoclonal antibody is an antibody directed to human NLGn4.

According to some embodiments, the antibody interferes with the binding of NLGn4 to NrX1b. According to some embodiments, the antibody is capable of reducing NLGn4 protein levels.

According to some embodiments, the NLGn4 antibody, or a fragment, derivative or analog thereof is capable of binding to the interaction domain of NLGn4, the interaction domain mediating the interaction between NLGn4 to NrX1b.

According to some embodiments, the anti-NLGn4 antibody or a fragment, derivative or analog thereof is capable of binding to amino acids 359-364, set forth in SEQ ID NO: 2 (QGEFLN), of the human NLGN4 protein.

According to some embodiments, the NLGn4 antibody, or a fragment, derivative or analog thereof is capable of binding to an epitope comprising the amino acid E361 of human NLGn4.

According to some embodiments, the NLGn4 antibody, or a fragment, derivative or analog thereof is is capable of binding to an epitope comprising the amino acid L363 of human NLGn4.

According to some embodiments, the NLGn4 antibody, or a fragment, derivative or analog thereof is capable of binding to an epitope within residues 261-270, set forth in SEQ ID NO: 3 (SLLTLSHYSE), of human NLGn4.

According to some embodiments, the NLGn4 antibody, or a fragment, derivative or analog thereof is capable of binding to an epitope comprising the amino acid H267 of human NLGn4.

According to some embodiments, the NLGn4 antibody, or a fragment, derivative or analog thereof is capable of binding to an epitope within residues 461-470, set forth in SEQ ID NO: 4 (AQYGSPTYFY), of human NLGn4.

According to some embodiments, the NLGn4 antibody, or a fragment, derivative or analog thereof is capable of binding to an epitope comprising the amino acid Y463 of human NLGn4.

According to some embodiments, the NLGn4 antibody, or a fragment, derivative or analog thereof is capable of binding to an epitope within residues 265-275, set forth in SEQ ID NO: 5 (LSHYSEGLFQK), of human NLGn4.

According to some embodiments, the NLGn4 antibody, or a fragment, derivative or analog thereof is capable of binding to an epitope comprising the amino acid E270 of human NLGn4.

According to some embodiments, the NLGn4 antibody, or a fragment, derivative or analog thereof is capable of binding to an epitope comprising an amino acid selected from the group consisting of E361, L363, H267, Y463, E270 or any combination thereof. Each possibility is a separate embodiment of the invention.

According to some embodiments, antibody is an antibody to human Nrx1b.

According to some embodiments, the Nrx1b monoclonal antibody, or a fragment, derivative or analog thereof is capable of binding to the interaction domain of Nrx1b, the interaction domain mediating the interaction between NLGn4 to NrX1b.

According to some embodiments, the anti-Nrx1b antibody or a fragment, derivative or analog thereof is capable of binding to amino acids 103-109, set forth in SEQ ID NO: 7 (LLADTPV) and/or amino acids 234-239 as set forth in SEQ ID NO: 7 (CSVVDD), of the human Nrxb1 protein. Each possibility is a separate embodiment of the invention.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the liver disorder is characterized by NLGn4 overexpression. According to some embodiments, NLGn4 overexpression comprises a 2, 3, 4, 5-10 fold or more increase in NLGn4 expression relative to the expression level obtained in normal subjects. Each possibility is a separate embodiment of the invention. According to some embodiments, the overexpression attenuates NK cell activity, inhibits the expression of NLGn4 and modulates and/or activates the function of the NK cell.

According to some embodiments, the liver disorder is NAFLD and/or hepatocellular carcinoma. According to some embodiments, the liver disorder is NAFLD. According to some embodiments, the liver disorder is hepatocellular carcinoma.

According to some embodiments, administering to the subject a therapeutically effective amount of a humanized, monoclonal antibody to NLGn4 and/or its receptor Nrx1b comprises administering the composition to an immune cell population of the subject.

According to some embodiments, administering a therapeutically effective amount of a humanized, monoclonal antibody to NLGn4 to a subject reduces the NLGn4 protein levels in the subject's NK cells. According to some embodiments, reducing NLGn4 protein levels in NK cells reduces the activity of hepatic stellate cells (also referred to herein as HSCs). According to some embodiments, reducing NLGn4 protein levels increases apoptosis of the hepatic stellate cells.

According to some embodiments, there is provided a humanized monoclonal antibody reactive with a human NLGN4. According to some embodiments, the human NLGn4 protein is a polypeptide sequence comprising SEQ ID NO: 1.

According to some embodiments, the anti-NLGn4 monoclonal antibody or a fragment, derivative or analog thereof is capable of binding to amino acids 359-364, set forth in SEQ ID NO: 2 (QGEFLN), of the human NLGN4 protein.

According to some embodiments, the NLGn4 monoclonal antibody, or a fragment, derivative or analog thereof is capable of binding to an epitope comprising the amino acid E361 of human NLGn4.

According to some embodiments, the NLGn4 monoclonal antibody, or a fragment, derivative or analog thereof is capable of binding to an epitope comprising the amino acid L363 of human NLGn4.

According to some embodiments, the NLGn4 monoclonal antibody, or a fragment, derivative or analog thereof is capable of binding to an epitope within residues 261-270, set forth in SEQ ID NO: 3 (SLLTLSHYSE), of human NLGn4.

According to some embodiments, the NLGn4 monoclonal antibody, or a fragment, derivative or analog thereof is capable of binding to an epitope comprising the amino acid H267 of human NLGn4.

According to some embodiments, the NLGn4 monoclonal antibody, or a fragment, derivative or analog thereof is capable of binding to an epitope within residues 461-470, set forth in SEQ ID NO: 4 (AQYGSPTYFY), of human NLGn4.

According to some embodiments, the NLGn4 monoclonal antibody, or a fragment, derivative or analog thereof is capable of binding to an epitope comprising the amino acid Y463 of human NLGn4.

According to some embodiments, the NLGn4 monoclonal antibody, or a fragment, derivative or analog thereof is capable of binding to an epitope within residues 265-275, set forth in SEQ ID NO: 5 (LSHYSEGLFQK), of human NLGn4.

According to some embodiments, the NLGn4 monoclonal antibody, or a fragment, derivative or analog thereof is capable of binding to an amino acid selected from the group consisting of E361, L363, H267, Y463, E270 or any combination thereof, of human NLGn4.

According to some embodiments, the NLGn4 monoclonal antibody, or a fragment, derivative or analog thereof is capable of reducing human NLGn4 protein levels.

According to some embodiments, the NLGn4 monoclonal antibody, or a fragment, derivative or analog thereof is capable of interfering with, inhibiting and/or preventing binding of NLGn4 to Nrx1b.

According to some embodiments, there is provided a composition comprising a therapeutically effective amount of an agent capable of interfering with, inhibiting and/or preventing NLGn4-Nrx1b protein-protein interaction and a pharmaceutically acceptable carrier. According to some embodiments, the composition is for the use of treating a liver disorder. According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention. According to some embodiments, the liver disorder is NAFLD and/or hepatocellular carcinoma. According to some embodiments, the liver disorder is NAFLD. According to some embodiments, the liver disorder is hepatocellular carcinoma.

According to some embodiments, the agent comprises recombinant NLGn4. According to some embodiments, the recombinant NLGn4 is soluble (rsNLGn4); wherein the rsNLGn4 comprises the extracellular domain of NLGn4 or a fragment, derivative or analog thereof.

According to some embodiments, the extracellular domain of NLGn4 consists of SEQ ID NO: 7. According to some embodiments, the rsNLGn4 consists of SEQ ID NO: 7, or a fragment, derivative or analog thereof.

According to some embodiments, the recombinant NLGn4 comprises Gln42-Ser676 of NP_065793. According to some embodiments, the recombinant NLGn4 consists essentially of Gln42-Ser676 of NP_065793.

According to some embodiments, the rsNLGn4 competes with endogenous NLGn4 for binding to Nrx1b.

According to some embodiments, the rsNLGn4 is devoid of the intracellular domain and/or the transmembrane domain of NLGn4.

According to some embodiments, the agent comprises a fusion protein comprising rsNLGn4 and an immunoglobulin molecule. According to some embodiments, the agent comprises a fusion protein comprising rsNLGn4 and an Fc domain of an immunoglobulin molecule. According to some embodiments, the Fc domain may include part or the entire CH1 domain, CH2 domain, CH3 domain and hinge region of IgG1, IgG2, IgG3 and IgG4. According to some embodiments, the Fc domain may be devoid of the CH1 domain. According to some embodiments, the Fc domain comprises Pro100-Lys330 of Human IgG1. According to some embodiments, the Fc domain consists essentially of Pro100-Lys330 of Human IgG1. According to some embodiments, the Fc domain may be linked to rsNLGn4 through a linker. According to some embodiments, the linker may include the amino acid sequence set forth in SEQ ID NO: 13 (IEGRMD).

According to some embodiments, the agent is a chimeric protein formed from NLGn4 polypeptides or fragments fused with a second polypeptide to form a soluble NLGn4. According to some embodiments, the agent comprises a DNA sequences, which combine two partial DNA sequences, one sequence encoding soluble fragments of NLGn4 (i.e. the DNA sequence encoding the extracellular domain of NLGn4) and the other partial sequence encoding all domains except the first domain of the constant region of the heavy chain of human immunoglobulin IgG, IgA, IgM, or IgE. These DNA sequences may subsequently be expressed in target cells using expression vectors as known in the art, thereby obtaining endogenous expression of recombinant proteins having the extracellular domain of NLGn4 joined to the Fc fragment of an immunoglobulin molecule.

According to some embodiments, NLGn4 is encoded by the sequence set forth in SEQ ID NO: 1.

According to some embodiments, the agent comprises recombinant Nrx1b. According to some embodiments, the recombinant Nrx1b is soluble (rsNrx1b); wherein the rsNrx1b comprises the extracellular domain of Nrx1b or a fragment, derivative or analog thereof capable of binding NLGn4.

According to some embodiments, the recombinant Nrx1b comprises Ala51-Ser363 of NP_620072. According to some embodiments, the recombinant Nrx1b consists essentially of Ala51-Ser363 of NP_620072.

According to some embodiments, the extracellular domain of Nrx1b consists of SEQ ID NO: 10. According to some embodiments, the rsNrx1b consists of SEQ ID NO: 10, or a fragment, derivative or analog thereof.

According to some embodiments, the rsNrx1b competes with endogenous Nrx1b for binding to NLGn4.

According to some embodiments, the rsNrx1b is devoid of the intracellular domain and/or the transmembrane domain of Nrx1b.

According to some embodiments, Nrx1b is encoded by the sequence set forth in SEQ ID NO: 6.

According to some embodiments, the agent comprises a fusion protein comprising rsNrx1b and an immunoglobulin molecule. According to some embodiments, the agent comprises a fusion protein comprising rsNrx1b and an Fc domain of an immunoglobulin molecule. According to some embodiments, the Fc domain may include part or the entire CH1 domain, the CH2 domain, the CH3 domain and hinge region of IgG1, IgG2, IgG3 and IgG4. According to some embodiments, the Fc domain may be devoid of the CH1 domain. According to some embodiments, the Fc domain may include all domains of the Fc domain apart from CH1. According to some embodiments, the Fc domain comprises Pro100-Lys330 of Human IgG1. According to some embodiments, the Fc domain consists essentially of Pro100-Lys330 of Human IgG1. According to some embodiments, the Fc domain may be linked to rsNrx1b through a linker. According to some embodiments, the linker may have the amino acid sequence set forth in SEQ ID NO: 13 (IEGRMD).

According to some embodiments, the agent is a chimeric protein formed from Nrx1b polypeptides or fragments fused with a second polypeptide to form a soluble Nrx1. According to some embodiments, the agent comprises a DNA sequences, which combine two partial DNA sequences, one sequence encoding soluble fragments of Nrx1b (i.e. the DNA sequence encoding the extracellular domain of Nrx1b) and the other partial sequence encoding all domains except the first domain of the constant region of the heavy chain of human immunoglobulin IgG, IgA, IgM, or IgE. These DNA sequences may subsequently be expressed in target cells using expression vectors as known in the art, thereby obtaining endogenous expression of recombinant proteins having the extracellular domain of Nrx1b joined to the Fc fragment of an immunoglobulin molecule.

According to some embodiments, the agent comprises recombinant NLGn4 and recombinant Nrx1b. According to some embodiments, the recombinant NlGn4 and Nrx1b are soluble (rsNLGN4 and rsNrx1b, respectively); wherein the rsNLGn4 comprises the extracellular domain of NLGN4 or a fragment, derivative or analog thereof capable of binding NLGn4; and wherein the rsNrx1b comprises the extracellular domain of Nrx1b or a fragment, derivative or analog thereof capable of binding NLGn4.

According to some embodiments, the agent is an antibody to NLGn4. According to some embodiments, the antibody is a monoclonal antibody. According to some embodiments, the agent is an antibody to Nrxb1. According to some embodiments, the antibody is a monoclonal antibody. According to some embodiments, the antibody is a humanized antibody. According to some embodiments, there is provided a composition comprising a therapeutically effective amount of monoclonal antibodies to NLGn4 and to Nrxb1.

According to some embodiments, the composition is for the use in treating, attenuating and/or preventing progression of a liver disorder in a subject.

According to some embodiments, the composition further comprises a GLUT4 antagonist. According to some embodiments, NLGn4 expression is regulated by a specific type of ionotropic glutamate receptor N-methyl-D-aspartate (NMDA or GLUT4 receptor; NMDAR). According to some embodiments, NLGn4 is linked to NMDR and both localize and bind PSD-95; a post synaptic density protein (PSD) According to some embodiments, the composition comprises an NMDAR antagonist selected from the group consisting of: Ketamin, Amantadine, Phencyclidine, Nitrous oxide, Dextromethorphan (and dextrorphan), Memantine, Ethanol, Riluzole, Xenon, HU-211, Lead (Pb2+), Conantokins, and Huperzine A.

According to an alternative embodiment, administering an N-methyl D aspartate receptor (NMDAR) agonist can increase NMDAR-mediated NLGn4 expression and as a result attenuate NK cell activity. Non-limiting examples of NMDAR agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

According to some embodiments, the pharmaceutical composition further comprises a pharmaceutically acceptable carrier.

According to some embodiments, there is provided method of treating, attenuating and/or preventing progression of a liver disorder in a subject, the method comprising administering to the subject in need thereof a therapeutically effective amount of an agent capable of interfering with, inhibiting and/or preventing neuroligin 4 (NLGn4)-Neurexin 1β (Nrx1b) protein-protein interaction; thereby treating, attenuating and/or preventing progression of the liver disorder.

According to some embodiments, there is provided composition for use in treating, attenuating and/or preventing progression of a liver disorder in a subject, the composition comprising a therapeutically effective amount of an agent capable of interfering with, inhibiting and/or preventing neuroligin 4 (NLGn4)-Neurexin 1β (Nrx1b) protein-protein interaction.

According to some embodiments, there is provided composition comprising a therapeutically effective amount of an agent capable of interfering with, inhibiting and/or preventing neuroligin 4 (NLGn4)-Neurexin 1β (Nrx1b) protein-protein interaction for use in treating, attenuating and/or preventing progression of a liver disorder.

According to some embodiments, there is provided an agent capable of interfering with, inhibiting and/or preventing neuroligin 4 (NLGn4)-Neurexin 1β (Nrx1b) protein-protein interaction for use in preparation of a composition for treating, attenuating and/or preventing progression of a liver disorder.

According to some embodiments, the agent comprises recombinant soluble NLGn4 (rsNLGn4); wherein the rsNLGn4 comprises the extracellular domain of NLGN4 or a fragment, derivative or analog thereof. According to some embodiments, the extracellular domain of NLGn4 consists of SEQ ID NO: 7 or a fragment, derivative or analog thereof. According to some embodiments, the rsNLGn4 competes with endogenous NLGn4 for binding to Nrx1b. According to some embodiments, the rsNLGn4 is devoid of the intracellular domain and/or transmembrane domain of NLGn4. According to some embodiments, NLGn4 is encoded by the sequence set forth in SEQ ID NO: 1. According to some embodiments, the agent comprises a fusion protein comprising the Fc portion of an immunoglobulin molecule and SEQ ID NO: 7 or a fragment thereof.

According to some embodiments, the therapeutic agent comprises recombinant soluble Nrx1b (rsNrx1b); wherein the rsNrx1b comprises the extracellular domain of Nrx1b or a fragment, derivative or analog thereof capable of binding the NLGn4. According to some embodiments, the extracellular domain of Nrx1b consists of SEQ ID NO: 10. According to some embodiments, the rsNrx1b consists of SEQ ID NO: 10, or a fragment, derivative or analog thereof. According to some embodiments, the rsNrx1b competes with endogenous Nrx1b for binding to NLGn4. According to some embodiments, the rsNrx1b is devoid of the intracellular domain and/or the transmembrane domain of Nrx1b. According to some embodiments, the Nrx1b is encoded by the sequence set forth in SEQ ID NO: 6. According to some embodiments, the agent comprises a fusion protein comprising the Fc portion of an immunoglobulin molecule and SEQ ID NO: 10 or a fragment thereof.

According to some embodiments, the therapeutic agent comprises an anti-NLGn4 antibody, or a fragment, derivative or analog thereof, comprising at least the antigen-binding portion thereof. According to some embodiments, the antibody is a humanized monoclonal anti-NLGn4 antibody. According to some embodiments, the anti-NLGn4 antibody is capable of binding specifically to an interaction domain of human NLGn4. According to some embodiments, the anti-NLGn4 antibody is capable of binding specifically to amino acids 359-364 of the human NLGN4 protein. According to some embodiments, the anti-NLGn4 antibody is capable of binding to an epitope within residues 261-270 of the human NLGn4, as set forth in SEQ ID NO: 3 (SLLTLSHYSE). According to some embodiments, the anti-NLGn4 antibody is capable of binding to an epitope within residues 265-275, as set forth in SEQ ID NO: 5 (LSHYSEGLFQK), of the human NLGn4. According to some embodiments, the anti-NLGn4 antibody is capable of binding to an epitope within residues 461-470 of the human NLGn4, as set forth in SEQ ID NO: 4 (AQYGSPTYFY).

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. According to some embodiments, the liver disorder is NAFLD. According to some embodiments, the liver disorder is hepatocellular carcinoma.

DETAILED DESCRIPTION

Figure 1:
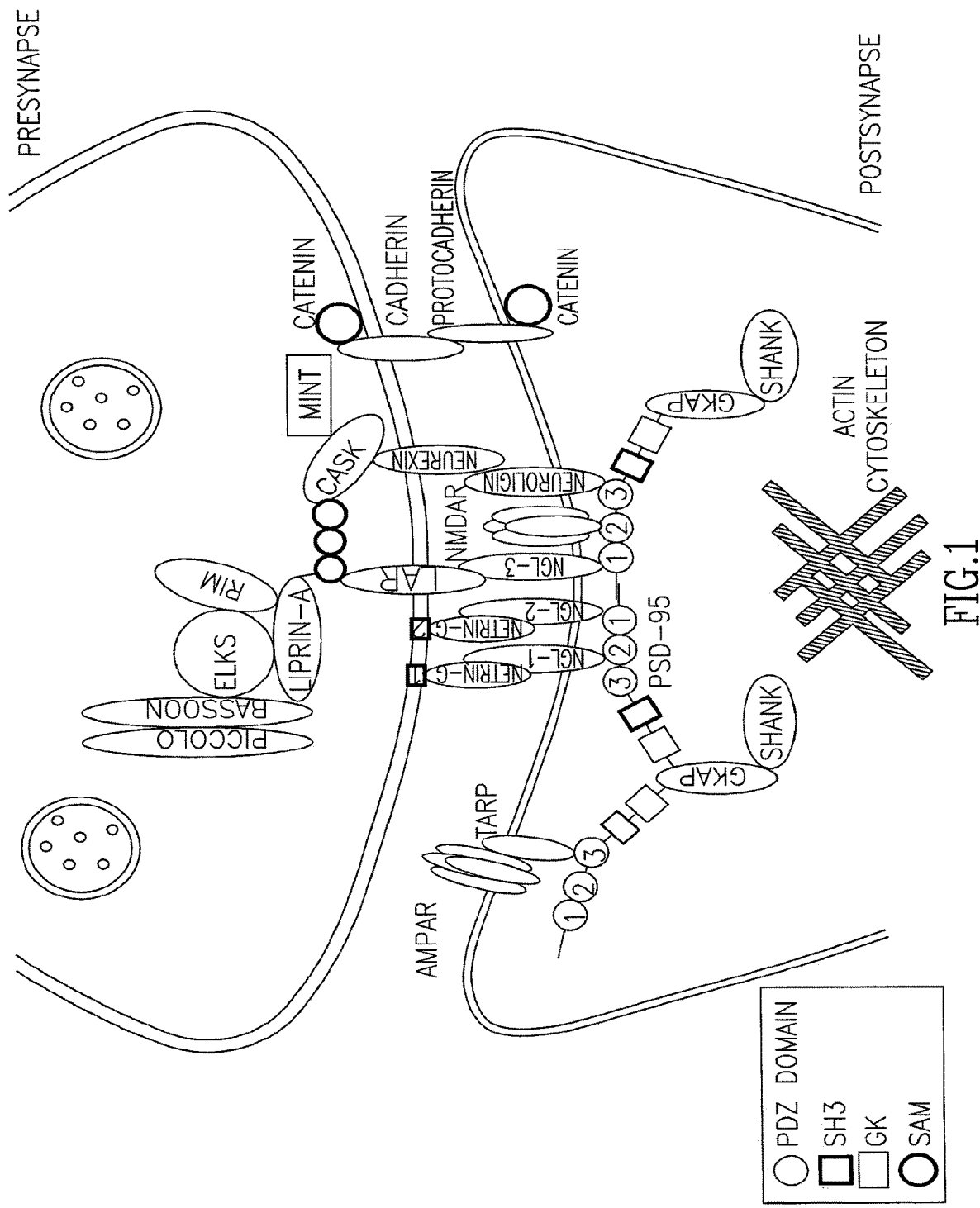
FIG. 1 shows a schematic representation of the Neuroligins and their interactions.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The following are terms which are used throughout the description and which should be understood in accordance with the various embodiments to mean as follows:

The terms "administration" and "administering" refer to providing or giving a subject a therapeutic agent (e.g. a recombinant polypeptide), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes. Each possibility is a separate embodiment.

The terms "peptide", "polypeptide" and "protein" as used herein are intended to encompass any amino acid sequence including modified sequences, such as but not limited to modified NLGn4 and/or Nrx1b. The terms "peptide" and "polypeptide" are specifically intended to cover naturally occurring proteins, as well as those, which are recombinantly or synthetically produced. "Peptides" of the invention also include modified peptides (with amino acid substitutions, both conservative and non-conservative as described below) that have the same or improved activity as a wild-type or unmodified peptide. "Salts" of the peptides of the invention contemplated by the invention are physiologically and pharmaceutically acceptable organic and inorganic salts.

Isolated polynucleotide sequences comprising at least one sequence encoding a peptide, peptide analog, conjugate or fusion protein of NLGn4 or Nrx1b are also included in the scope of the present invention. According to some embodiments, the polynucleotide sequence encoding the peptide or peptide analog is translationally linked to another polynucleotide sequence such as an RNA or DNA molecule and is recombinantly expressed within target cells. According to other embodiments, the polynucleotide sequence is part of a recombinant viral or bacterial vector.

The term "analog" refers to a molecule, which has the amino acid sequence according to the invention except for one or more amino acid changes. Analogs according to the present invention may include peptidomimetics. "Peptidomimetic" refers to a peptide modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with another covalent bond. A peptidomimetic according to the present invention may optionally comprise at least one bond, which is an amide-replacement bond such as urea bond, carbamate bond, sulfonamide bond, hydrazine bond, or any other covalent bond. The design of appropriate "analogs" may be computer assisted. Analogs are included in the invention as long as they remain pharmaceutically acceptable.

The amino acids used in this invention are those, which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration into the islets, targeting to specific beta cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W).

The peptides of the present invention may be produced by any method known in the art, including recombinant and synthetic methods. Synthetic methods include exclusive solid phase synthesis, partial solid phase synthesis, fragment condensation, or classical solution synthesis. Solid phase peptide synthesis procedures are well known to one skilled in the art and described, for example by John Morrow Stewart and Janis Dillaha Young, Solid Phase Polypeptide Syntheses (2nd Ed., Pierce Chemical Company, 1984). In some embodiments, synthetic peptides are purified by preparative high performance liquid chromatography (Creighton T. (1983) Proteins, structures and molecular principles. WH Freeman and Co. N.Y.) The peptide sequence may be confirmed by amino acid sequencing using methods known to one skilled in the art.

In some embodiments, recombinant protein techniques are used to generate the peptide of the present invention. In some embodiments, recombinant protein techniques are used for generation of relatively long polypeptides (typically longer than 18 amino acids) or nucleic acid sequences or viral or bacterial vectors for vaccine formulation. Recombinant techniques are described for example by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

The terms "recombinant" and "recombinant protein" refer, according to some embodiments, to proteins having sequence that is not naturally occurring. The term recombinant includes proteins that have been altered by addition, substitution, or deletion of a portion of a natural nucleic acid molecule or protein. According to some embodiments, the term recombinant refers to proteins that have been altered so as to generate soluble forms of NLGn4 and/or NRx1b.

As used herein, the term "soluble" refers to a polypeptide that is not bound to the cell membrane. Usually, a receptor is in soluble form when its amino acid sequence lacks the transmembrane domain. In this context, a form will be soluble if using conventional assays known to one of skill in the art most of this form can be detected in fractions that are not associated with the membrane, e.g., in cellular supernatants or serum.

In the present invention, "Fc domain" means the constant domain of an antibody. It is preferably the Fc domain of human IgG1, but is not limited thereto. In addition to human IgG1, IgG2, IgG3 and IgG4 may also be used, and the Fc domain may comprise. Preferably, it may comprise the CH2 domain, the CH3 domain and the hinge region, excluding the CH1 domain.

As used herein, the term "NLGn4-Fc fusion protein" refers to a product resulting from linkage of the entire or a part of the NLGn4 protein with immunoglobulin Fc region (or part thereof). As used herein, the term "rsNLGn4-Fc fusion protein" refers to a product resulting from linkage of the extracellular domain of NLGn4 protein with immunoglobulin Fc region (or part thereof). The linkage may be by enzymatic action, or resulting from expression of two polypeptides into a single polypeptide by gene manipulation. In the NLGn4-Fc and rsNLGn4-Fc fusion proteins, the NLGn4 protein (or part thereof) and the immunoglobulin Fc region may be directly linked with each other, or linked via a peptide linker, but is not limited thereto.

As used herein, the term "Nrx1b-Fc fusion protein" refers to a product resulting from linkage of the entire or a part of the Nrx1b protein with immunoglobulin Fc region (or part thereof). As used herein, the term "rsNrx1b-Fc fusion protein" refers to a product resulting from linkage of the extracellular domain of Nrx1b protein with immunoglobulin Fc region (or part thereof). The linkage may be by enzymatic action, or resulting from expression of two polypeptides into a single polypeptide by gene manipulation. In the Nrx1b-Fc and rsNrx1b fusion proteins, the Nrx1b protein (or part thereof) and the immunoglobulin Fc region may be directly linked with each other, or linked via a peptide linker, but is not limited thereto.

As used herein, the term "immunoglobulin (Ig) Fc region" refers to a part of immunoglobulin that contains the heavy-chain constant region 2 (CH2), the heavy-chain constant region 3 (CH3), and a hinge region, excluding the variable regions of the heavy and light chains, the heavy-chain constant region 1 (CH1) and the light-chain constant region 1 (CL1) of the immunoglobulin. The immunoglobulin Fc region of the present invention includes a native amino acid sequence, and a sequence derivative thereof. In addition, the immunoglobulin Fc region may be an Fc region that is derived from IgG, IgM, IgE, IgA or IgD, or that is made by combinations thereof or hybrids thereof. Preferably, it is derived from IgG, which is known to enhance the half-life of binding proteins. More preferably, it is derived from IgG1, but is not limited thereto.

The Ig combinations, as used herein, refer to polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

Ig hybrids, as used herein, refer to sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region. On the other hand, IgG is also divided into IgG1, IgG2, IgG3 and IgG4 subclasses, and the present invention includes combinations and hybrids thereof.

The term "sequence identity/similarity" refers to the degree of similarity between two or more nucleic acid sequences, or two or more amino acid sequences, and is measured as percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

The terms "liver disorder", "liver disease" and "hepatic disease" are used interchangeably and refer to diseases and disorders that cause the liver to function improperly or to stop functioning.

The terms "subject" and "patient" are interchangeable and as used herein refer to any individual suffering from a liver disorder.

The term "treatment" as used herein refers to both therapeutic treatment and prophylactic or preventative measures. Those in need of treatment include those already with the disorder as well as those in which the disorder is to be prevented.

The terms "composition" and "pharmaceutical composition" are used interchangeably and as used herein refer to any composition comprising at least one chemical or biological agent, for example an antibody.

The term "pharmaceutically acceptable carrier" refer to any carrier conventional used in the production of pharmaceutical compositions. Remington's Pharmaceutical Sciences, by E. W. Martin, Mack Publishing Co., Easton, Pa., 15th Edition, 1975, describes compositions and formulations suitable for pharmaceutical delivery of the compositions disclosed herein.

The terms "Neuroligin 4", "Neuroligin 4X", "NLGn4" and "NLG4" are interchangeable and as used herein refer to the protein product of the NLGn4 gene e.g., NP_001269075.1, NP_001269074.1, NP_851849.1 and NP_065793.1.

The terms "anti-NLGn4 antibody", "an antibody which recognizes NLGn4", "an antibody against NLGn4" and "an antibody to NLGn4" are interchangeable, and as used herein refer to an antibody that binds to the NLGn4 protein with sufficient affinity and specificity. According to some embodiments, the term refer to an antibody capable of interfering, inhibiting and/or preventing with NLGn4 binding to Nrx1b.

The terms "neurexin-1-beta", "Nrx1b" and "Nrxn1" are interchangeable and as used herein refer to the protein product of the Nrx1b gene e.g., NP_001129131.1 NP_004792.1 NP_620072.1.

The terms "anti-Nrx1b antibody", "an antibody which recognizes Nrx1b", "an antibody against Nrx1b" and "an antibody to Nrx1b" are interchangeable, and as used herein refer to an antibody that binds to the Nrx1b protein with sufficient affinity and specificity. According to some embodiments, the term refer to an antibody capable of interfering with, inhibiting and/or preventing Nrx1b binding to NLGn4.

It should be understood that, according to the present invention, anti-human-NLGn4 antibodies and/or anti-human-Nrx1b antibodies may bind to NLGn4 and/or Nrx1b both in-vivo, i.e. bind NLGn4/Nrx1b in a patient's NK cells, and/or bind NLGn4/Nrx1b in NK cells in-vitro, i.e. bind NLGn4/Nrx1b in NK cells extracted from the patient's body, the NK cells later administered to the patient.

The term "antigen" as used herein refers to a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies, which may be evoked by other antigens. According to some embodiments, the antigen is an NLGn4 protein or a fragment thereof. According to some embodiments, the antigen is an Nrx1b protein or a fragment thereof.

The term "antigenic determinant" or "epitope" as used herein refers to the region of an antigen molecule that specifically reacts with a particular antibody. Peptide sequences derived from an epitope can be used, alone or in conjunction with a carrier moiety, applying methods known in the art, to immunize animals and to produce polyclonal or monoclonal antibodies. Isolated peptides derived from an epitope may be used in diagnostic methods to detect antibodies and as therapeutic agents when inhibition of antibodies is required.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term $F(ab')_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively).

The light chain is either of two isotypes (kappa, κ or lambda, λ) found in all antibody classes.

The term "antibody" is used in the broadest sense and includes monoclonal antibodies (including full length or intact monoclonal antibodies), polyclonal antibodies, multivalent antibodies, multi-specific antibodies (e.g., bi-specific antibodies), and antibody fragments long enough to exhibit the desired biological activity.

The antibody according to the present invention is a molecule comprising at least the antigen-binding portion of an antibody. Antibody or antibodies according to the invention include intact antibodies, such as polyclonal antibodies or monoclonal antibodies (mAbs), as well as proteolytic fragments thereof, such as the Fab or F(ab')$_2$ fragments. Single chain antibodies also fall within the scope of the present invention.

"Antibody fragments" comprise only a portion of an intact antibody, generally including an antigen-binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

The term "neutralizing antibody" as used herein refers to a molecule having an antigen-binding site to a specific receptor or ligand target capable of reducing or inhibiting (blocking) activity or signaling through a receptor, as determined by in-vivo or in-vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs of the present invention may be of any immunoglobulin class including IgG, IgM, IgE, IgA. A hybridoma producing a mAb may be cultivated in-vitro or in-vivo. High titers of mAbs can be obtained by in-vivo production where cells from the individual hybridomas are injected intraperitoneally (i.p.) into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

The terms "human antibody" and "humanized antibody" are interchangeable and as used herein refer to an antibody that possesses an amino acid sequence, which corresponds to that of an antibody produced by a human and/or has been made using any of the techniques for making human antibodies as disclosed herein.

The terms "molecule having the antigen-binding portion of an antibody" and "antigen-binding-fragments" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')2 fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific mini-antibodies (see Muller et al., 1998) and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

The phrase "capable of inhibiting or blocking the interaction" as used herein refers to the capability of an agent, for example an antibody, to interact with a at least one target, for example a cell's membrane-bound receptor, in such a way that the target becomes less accessible, preferably inaccessible, to binding by at least one other agent, for example the receptor's natural antigen.

Antibodies according to the invention can be obtained by administering NLGn4 or Nrx1b peptides, analogs, or cells expressing these, to an animal, preferably a nonhuman, using routine protocols. For preparation of mAbs, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in Monoclonal Antibodies And Cancer Therapy, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Moreover, affinity maturation (i.e., increasing the affinity and specificity) of recombinant antibodies is very simple and relatively fast. Finally, large numbers of different antibodies against a specific antigen can be generated in one selection procedure. To generate recombinant mAbs one can use various methods all based on display libraries to generate a large pool of antibodies with different antigen recognition sites. Such a library can be made in several ways: One can generate a synthetic repertoire by cloning synthetic CDR regions in a pool of H chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity.

Non-human antibodies may be humanized by any methods known in the art. In one method, the non-human CDRs are inserted into a human antibody or consensus antibody FR sequence. Further changes can then be introduced into the antibody framework to modulate affinity or immunogenicity.

Anti-idiotype antibodies specifically immunoreactive with an antibody of the invention are also comprehended.

Techniques for the production of single-chain antibodies can be adapted to produce single-chain antibodies to polypeptides or polynucleotides of this invention. Also, transgenic mice, or other organisms such as other mammals, can be used to express humanized antibodies specific to the polypeptides or polynucleotides of the invention.

The invention also provides conservative amino acid variants of the peptides and antibody molecules according to the invention. Variants according to the invention also may be made that conserve the overall molecular structure of the encoded proteins or peptides. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

A humanized antibody, typically has a human FR grafted with non-human CDRs. Thus, a humanized antibody has one or more amino acid sequence introduced into it from a source, which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies wherein substantially less than an intact human V domain has been substituted by the corresponding sequence from a non-human species. In practice, humanized antibodies are typically human antibodies in which some CDR residues and possibly some FR residues are substituted by residues from analogous sites in rodent antibodies.

The choice of human VH and VL domains to be used in making the humanized antibodies is very important for reducing immunogenicity. According to the so-called "best-fit" method, the sequence of the V domain of a rodent antibody is screened against the entire library of known human-domain sequences. The human sequence, which is closest to that of the rodent, is then accepted as the human FR for the humanized antibody (Sims et al., J. Immunol., 151:2296 (1993); Chothia et al., J. Mol. Biol., 196:901 (1987)). Another method uses a particular FR derived from the consensus sequence of all human antibodies of a particular subgroup of H or L chains. It is further important that antibodies be humanized with retention of high specificity and affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

According to some aspects, the present invention provides methods and compositions for treating liver disorders by activating attenuated natural killer (NK) cells and thereby reducing Hepatic stellate cell (HCSs) induced fibrosis and/or hepatocellular carcinoma.

According to some aspects, the present invention provides a composition for use in treating liver disorders, the composition comprising an agent capable of activating attenuated natural killer (NK) cells, thereby reducing Hepatic stellate cell (HCSs) induced fibrosis and/or hepatocellular carcinoma.

According to some embodiments, the method includes administering to the subject in need thereof a therapeutically effective amount of an agent capable of interfering with, inhibiting and/or preventing neuroligin 4 (NLGn4)-Neurexin 1β (Nrx1b) protein-protein interaction; thereby treating, attenuating and/or preventing progression of the liver disorder. According to some embodiments, the composition comprises a therapeutically effective amount of an agent capable of interfering with, inhibiting and/or preventing neuroligin 4 (NLGn4)-Neurexin 1β (Nrx1b) protein-protein interaction. According to some embodiments, the composition is suitable for administration to a subject.

According to some embodiments, the agent comprises recombinant soluble NLGn4 (rsNLGn4).

According to some embodiments, the recombinant soluble human NLGn4 may function as a decoy competing with endogenous NLGn4 for binding to Nrx1b.

According to some embodiments, the recombinant NLGn4 comprises Gln42-Ser676 of NP_065793. According to some embodiments, the recombinant NLGn4 consists essentially of Gln42-Ser676 of NP_065793.

According to some embodiments, the rsNLGn4 comprises the extracellular domain of NLGn4, the extracellular domain of NLGn4 having the polypeptide sequence set forth in SEQ ID: 7.

SEQ ID NO: 7:
QAQYPVVNTNYGKIRGLRTPLPNEILGPVEQYLGVPYASPPTGERRFQPP

EPPSSWTGIRNTTQFAAVCPQHLDERSLLHDMLPIWFTANLDTLMTYVQD

QNEDCLYLNIYVPTEDDIHDQNSKKPVMVYIHGGSYMEGTGNMIDGSILA

SYGNVIVITINYRLGILGFLSTGDQAAKGNYGLLDQIQALRWIEENVGAF

GGDPKRVTIFGSGAGASCVSLLTLSHYSEGLFQKAIIQSGTALSSWAVNY

QPAKYTRILADKVGCNMLDTTDMVECLRNKNYKELIQQTITPATYHIAFG

PVIDGDVIPDDPQILMEQGEFLNYDIMLGVNQGEGLKFVDGIVDNEDGVT

PNDFDFSVSNFVDNLYGYPEGKDTLRETIKFMYTDWADKENPETRRKTLV

ALFTDHQWVAPAVATADLHAQYGSPTYFYAFYHHCQSEMKPSWADSAHGD

EVPYVFGIPMIGPTELFSCNFSKNDVMLSAVVMTYWINFAKTGDPNQPVP

QDTKFIHTKPNRFEEVAWSKYNPKDQLYLHIGLKPRVRDHYRATKVAFWL

ELVPHLHNLNEIFQYVSTITKVPPPDMTSFPYGTRRSPAKIWPTTKRPAI

TPANNPKHSKDPHKTGPEDTTVLIETKRDYSTELS

According to some embodiments, the rsNLGn4 consists of SEQ ID NO: 7, or a fragment, derivative or analog thereof. According to some embodiments, the rsNLGn4 has at least 70%, at least 80%, at least 90%, at least 95% or at least 98% sequence similarity to SEQ ID NO: 7. Each possibility is separate embodiment.

According to some embodiments, the rsNLGn4 is devoid of the intracellular domain of NLGn4 set forth in SEQ ID NO: 8:

SEQ ID NO: 8:
YKKDKRRHETHRRPSPQRNTTNDIAHIQNEEIMSLQMKQLEHDHECESLQ

AHDTLRLTCPPDYTLTLRRSPDDIPLMTPNTITMIPNTLTGMQPLHTFNT

FSGGQNSTNLPHGHSTTRV

According to some embodiments, the rsNLGn4 is devoid of the transmembrane domain of NLGn4 set forth in SEQ ID NO: 9:

SEQ ID NO: 9:
VTIAVGASLLFLNILAFAALY

According to some embodiments, the agent comprises recombinant soluble Nrx1b (rsNrx1b).

According to some embodiments, the recombinant Nrx1b comprises Ala51-Ser363 of NP_620072. According to some embodiments, the recombinant Nrx1b consists essentially of Ala51-Ser363 of NP_620072.

According to some embodiments, recombinant soluble human Nrx1b may function as a decoy competing with endogenous Nrx1b for binding to NLGn4.

According to some embodiments, the rsNrx1b comprises the extracellular domain of Nrx1b, the extracellular domain of Nrx1b having the polypeptide sequence set forth in SEQ ID: 10.

SEQ ID NO: 10:
ASSLGAHHIHHFHGSSKHHSVPIAIYRSPASLRGGHAGTTYIFSKGGGQI

TYKWPPNDRPSTRADRLAIGFSTVQKEAVLVRVDSSSGLGDYLELHIHQG

KIGVKFNVGTDDIAIEESNAIINDGKYHVVRFTRSGGNATLQVDSWPVIE

RYPAGRQLTIFNSQATIIIGGKEQGQPFQGQLSGLYYNGLKVLNMAAEND

ANIAIVGNVRLVGEVPSSMTTESTATAMQSEMSTSIMETTTTLATSTARR

GKPPTKEPISQTTDDILVASAECPSDDEDIDPCEPSSGGLANPTRAGGRE

PYPGSAEVIRESS

According to some embodiments, the rsNrx1b consists of SEQ ID NO: 10, or a fragment, derivative or analog thereof. According to some embodiments, the rsNrx1b has at least 70%, at least 80%, at least 90%, at least 95% or at least 98% sequence similarity to SEQ ID NO: 10. Each possibility is separate embodiment.

According to some embodiments, the rsNrx1b is devoid of the intracellular domain of Nrx1b set forth in SEQ ID NO: 11:

SEQ ID NO: 11:
MYKYRNRDEGSYHVDESRNYISNSAQSNGAVVKEKQPSSAKSSNKNKKNK
DKEYYV

According to some embodiments, the rsNrx1b is devoid of the transmembrane domain of NLGn4 set forth in SEQ ID NO: 12:

SEQ ID NO: 12:
STTGMVVGIVAAAALCILILLYA

According to some embodiments, the agent comprises a combination of recombinant soluble NLGn4 and recombinant soluble Nrx1b (rsNrx1b).

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof.

According to some embodiments, of the agent comprises an anti-NLGn4 antibody.

According to some embodiments, administering a therapeutically effective amount of the agent includes contacting an immune cell, such as an NK cell and/or a $CD56^{dim}$ NK cell subset, with the therapeutically effective amount of the agent.

According to some embodiments, the antibody is a monoclonal antibody. According to some embodiments, the antibody is a humanized antibody. According to some embodiments, the antibody does not cross the blood-brain barrier (BBB).

According to some embodiments, the antibody is an anti-NLGn4 monoclonal antibody or a fragment, derivative or analog thereof.

According to some embodiments, the polypeptide sequence of the NLGn4 is set forth in SEQ ID NO: 1:

MSRPQGLLWLPLLFTPVCVMLNSNVLLWLTALAIKFTLIDSQAQYPVVNT

NYGKIRGLRTPLPNEILGPVEQYLGVPYASPPTGERRFQPPEPPSSWIGI

RNTTQFAAVCPQHLDERSLLHDMLPIWFTANLDTLMTYVQDQNEDCLYLN

IYVPTEDDIHDQNSKKPVMVYIHGGSYMEGTGNMIDGSILASYGNVIVIT

INYRLGILGFLSTGDQAAKGNYGLLDQIQALRWIEENVGAFGGDPKRVTI

FGSGAGASCVSLLTLSHYSEGLFQKAIIQSGTALSSWAVNYQPAKYTRIL

ADKVGCNMLDTTDMVECLRNKNYKELIQQTITPATYHIAFGPVIDGDVIP

DDPQILMEQGEFLNYDIMLGVNQGEGLKFVDGIVDNEDGVTPNDFDFSVS

NFVDNLYGYPEGKDTLRETIKFMYTDWADKENPETRRKTLVALFTDHQWV

APAVATADLHAQYGSPTYFYAFYHHCQSEMKPSWADSAHGDEVPYVFGIP

MIGPTELFSCNFSKNDVMLSAVVMTYWINFAKTGDPNQPVPQDTKFIHTK

PNRFEEVAWSKYNPKDQLYLHIGLKPRVRDHYRATKVAFWLELVPHLHNL

NEIFQYVSTITKVPPPDMTSFPYGTRRSPAKIWPTTKRPAITPANNPKHS

KDPHKTGPEDTTVLIETKRDYSTELSVTIAVGASLLFLNILAFAALYYKK

DKRRHETHRRPSPQRNTTNDIAHIQNEEIMSLQMKQLEHDHECESLQAHD

TLRLTCPPDYTLTLRRSPDDIPLMTPNTITMIPNTLTGMQPLHTFNTFSG

GQNSTNLPHGHSTTRV

According to some embodiments, the NLGn4 monoclonal antibody, or a fragment, derivative or analog thereof is capable of binding to the interaction domain of NLGn4, mediating the interaction between NLGn4 and NrX1b.

According to some embodiments, the anti-NLGn4 monoclonal antibody or a fragment, derivative or analog thereof is capable of binding to amino acids 359-364 of the human NLGN4 protein as set forth in SEQ ID NO: 2 (QGEFLN).

According to some embodiments, the NLGn4 antibody, or a fragment, derivative or analog thereof is capable of binding to an epitope comprising the amino acid E361 of human NLGn4.

According to some embodiments, the NLGn4 antibody, or a fragment, derivative or analog thereof is capable of binding to an epitope comprising the amino acid L363 of human NLGn4.

According to some embodiments, the NLGn4 antibody, or a fragment, derivative or analog thereof is capable of binding to an epitope within residues 261-270, as set forth in SEQ ID NO: 3 (SLLTLSHYSE), of human NLGn4.

According to some embodiments, the NLGn4 antibody, or a fragment, derivative or analog thereof is capable of binding to an epitope comprising the amino acid H267 of human NLGn4.

According to some embodiments, the NLGn4 antibody, or a fragment, derivative or analog thereof is capable of binding to an epitope within residues 461-470, as set forth in SEQ ID NO: 4 (AQYGSPTYFY), of human NLGn4.

According to some embodiments, the NLGn4 antibody, or a fragment, derivative or analog thereof is capable of binding to an epitope comprising the amino acid Y463 of human NLGn4.

According to some embodiments, the NLGn4 antibody, or a fragment, derivative or analog thereof is capable of binding to an epitope within residues 265-275, as set forth in SEQ ID NO: 5 (LSHYSEGLFQK), of human NLGn4.

According to some embodiments, the NLGn4 antibody, or a fragment, derivative or analog thereof is capable of binding to an epitope comprising the amino acid E270 of human NLGn4.

According to some embodiments, the NLGn4 antibody, or a fragment, derivative or analog thereof is capable of binding to an epitope comprising an amino acid selected from the group consisting of E361, L363, H267, Y463, E270 or any combination thereof. Each possibility is a separate embodiment.

According to some embodiments, the antibody is an anti-Nrx1b antibody or a fragment, derivative or analog thereof. According to some embodiments, the Nrx1b antibody, or a fragment, derivative or analog thereof is capable of binding to the interaction domain of Nrx1b, mediating the interaction between NLGn4 to NrX1b.

According to some embodiments, the polypeptide sequence of the Nrx1b is set forth in SEQ ID NO: 6:

MGTALLQRGGCFLLCLSLLLLGCWAELGSGLEFPGAEGQWTRFPKWNACC

ESEMSFQLKTRSARGLVLYFDDEGFCDFLELILTRGGRLQLSFSIFCAEP

ATLLADTPVNDGAWHSVRIRRQFRNTTLFIDQVEAKWVEVKSKRRDMTVF

SGLFVGGLPPELRAAALKLTLASVREREPFKGWIRDVRVNSSQVLPVDSG

EVKLDDEPPNSGGGSPCEAGEEGEGGVCLNGGVCSVVDDQAVCDCSRTGF

RGKDCSQEIKFGLQCVLPVLLHDNDQGKYCCINTAKPLTEKDNNVEGLAH

LMMGDQGKSKGKEEYIATFKGSEYFCYDLSQNPIQSSSDEITLSFKTLQR

NGLMLHTGKSADYVNLALKNGAVSLVINLGSGAFEALVEPVNGKFNDNAW

HDVKVTRNLRQHSGIGHAMVNKLHCSVTISVDGILTTTGYTQEDYTMLGS

DDFFYVGGSPSTADLPGSPVSNNFMGCLKEVVYKNNDVRLELSRLAKQGD

PKMKIHGVVAFKCENVATLDPITFETPESFISLPKWNAKKTGSISFDFRT

TEPNGLILFSHGKPRHQKDAKHPQMIKVDFFAIEMLDGHLYLLLDMGSGT

IKIKALLKKVNDGEWYHVDFQRDGRSGTISVNTLRTPYTAPGESEILDLD

DELYLGGLPENKAGLVFPTEVWTALLNYGYVGCIRDLFIDGQSKDIRQMA

EVQSTAGVKPSCSKETAKPCLSNPCKNNGMCRDGWNRYVCDCSGTGYLGR

SCEREATVLSYDGSMFMKIQLPVVMHTEAEDVSLRFRSQRAYGILMATTS

RDSADTLRLELDAGRVKLTVNLDCIRINCNSSKGPETLFAGYNLNDNEWH

TVRVVRRGKSLKLTVDDQQAMTGQMAGDHTRLEFHNIETGIITERRYLSS

VPSNFIGHLQSLTFNGMAYIDLCKNGDIDYCELNARFGFRNIIADPVTFK

TKSSYVALATLQAYTSMHLFFQFKTTSLDGLILYNSGDGNDFIVVELVKG

YLHYVFDLGNGANLIKGSSNKPLNDNQWHNVMISRDTSNLHTVKIDTKIT

TQITAGARNLDLKSDLYIGGVAKETYKSLPKLVHAKEGFQGCLASVDLNG

RLPDLISDALFCNGQIERGCEGPSTTCQEDSCSNQGVCLQQWDGFSCDCS

MTSFSGPLCNDPGITYIFSKGGGQITYKWPPNDRPSTRADRLAIGFSTVQ

-continued

```
KEAVLVRVDSSSGLGDYLELHIHQGKIGVKFNVGTDDIAIEESNAIINDG

KYHVVRFTRSGGNATLQVDSWPVIERYPAGNNDNERLAIARQRIPYRLGR

VVDEWLLDKGRQLTIFNSQATIIIGGKEQGQPFQGQLSGLYYNGLKVLNM

AAENDANIAIVGNVRLVGEVPSSMTTESTATAMQSEMSTSIMETTTTLAT

STARRGKPPTKEPISQTTDDILVASAECPSDDEDIDPCEPSSGGLANPTR

AGGREPYPGSAEVIRESSSTTGMVVGIVAAAALCILILLYAMYKYRNRDE

GSYHVDESRNYISNSAQSNGAVVKEKQPSSAKSSNKNKKNKDKEYYV
```

According to some embodiments, the anti-Nrx1b monoclonal antibody or a fragment, derivative or analog thereof is capable of binding to amino acids 103-109 as set forth in SEQ ID NO: 7 (LLADTPV) and/or amino acids 234-239 as set forth in SEQ ID NO: 8 (CSVVDD) of the human Nrx1b protein. Each possibility is a separate embodiment of the invention.

According to some embodiments, the liver disorders is Non-alcoholic fatty liver disease (NAFLD), and Non-alcoholic steatohepatitis (NASH). Additionally or alternatively as the liver disorder is cirrhosis, hepatitis, liver adenoma, insulin resistance, liver cancer, or any NK related inflammatory or neoplastic disorder well. The clinical implications of NAFLD are derived mostly from its potential to progress to Non-alcoholic steatohepatitis, cirrhosis and liver failure. In accordance, the invention, addresses the long felt need to attenuate the progression of NAFLD into cirrhosis and liver failure by inhibiting, attenuating and/or preventing NLGn4-Nrx1b protein-protein interaction and thereby modulating the cytotoxic activity of NK cells. According to some embodiments, the invention provides a method for modulating the activity of a natural killer (NK) cell.

According to some embodiments, the NK cells are liver NK cells, which are attenuated in patients having a liver disorder. According to yet another embodiment, the liver disorder is characterized by overexpression of NLGn4 protein. Such overexpression can attenuate NK cell activity.

According to some embodiments and without being bound to any theory, reducing NLGn4 protein levels and/or interfering with the binding of NLGn4 to Nrx1b, modulates the function of the NK cell for example by activating the NK cell and/or the $CD56^{dim}$ NK cell subset. As a result of NK activation, the activity of hepatic stellate cells (HSCs) and hence fibrosis is reduced. In addition, and according to yet another embodiment, modulating and/or activating the NK cells increases the apoptosis of the HSCs.

According to yet another embodiment there is provided a method for modulating the activity of a natural killer (NK) cell and/or treating, preventing and/or attenuating a liver disorder by administering to a patient a composition comprising an anti-NLGn4 antibody and/or an anti-Nrx1b antibody.

According to some embodiments, the composition may further include a GLUT4 antagonist. Such antagonist can according to the present invention inhibit GLUT4 mediated NLGn4 expression. The antagonist can be selected from the group comprising Ketamine, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A.

Without being bound to any theory, reducing NLGn4 protein levels and/or inhibiting NLGn4-Nrx1b binding can, according to the present invention, enhances the cytotoxicity of the NK cells and/or specific NK cell subpopulations. According to certain embodiments, and without being bound to any theory, enhancing the cytotoxicity comprises enhancing the expression of CD107a (marker of NK cell functional activity) on said NK cell.

In certain liver disorders, NK cell function can be attenuated. According to the present invention and without being bound by any theory, such attenuation can be a result of NLGn4 overexpression. In accordance, reducing NLGn4 protein levels modulates and/or activates the function of attenuated NK cell. In turn, activating the NK cell may reduce HSC activity and/or increase their apoptosis.

As further demonstrated herein below, it has now surprisingly been shown that administration of anti-NLGn4 antibodies, increases NK cell activity and attenuates HSC activation, both in-vitro and in-vivo. These results show that anti-NLGn4 antibodies can serve as therapeutically agents in the treatment of liver disorders such as but not limited to NAFLD and preventing its progression to cirrhosis.

According to some embodiments, there is provided a composition comprising a therapeutically effective amount of an agent capable of interfering with, inhibiting and/or preventing neuroligin 4 (NLGn4)-Neurexin 1β (Nrx1b) protein-protein interaction and a pharmaceutically acceptable carrier.

According to some embodiments, the recombinant NLGn4 comprises Gln42-Ser676 of NP_065793. According to some embodiments, the recombinant NLGn4 consists essentially of Gln42-Ser676 of NP_065793.

According to some embodiments, the agent comprises recombinant soluble NLGn4 (rsNLGn4); wherein the rsNLGn4 comprises the extracellular domain of NLGn4 or a fragment, derivative or analog thereof.

According to some embodiments, the extracellular domain of NLGn4 consists of SEQ ID NO: 7. According to some embodiments, the rsNLGn4 consists of SEQ ID NO: 7, or a fragment, derivative or analog thereof.

According to some embodiments, the rsNLGn4 competes with endogenous NLGn4 for binding to Nrx1b.

According to some embodiments, the rsNLGn4 is devoid of the intracellular domain and/or the transmembrane domain of NLGn4.

According to some embodiments, the agent comprises a fusion protein comprising rsNLGn4 and an immunoglobulin molecule. According to some embodiments, the agent comprises a fusion protein comprising rsNLGn4 and an Fc domain of an immunoglobulin molecule. According to some embodiments, the Fc domain may include part or the entire CH1 domain, CH2 domain, CH3 domain and hinge region of IgG1, IgG2, IgG3 and IgG4. According to some embodiments, the Fc domain may be devoid of the CH1 domain. According to some embodiments, the Fc domain comprises Pro100-Lys330 of Human IgG1. According to some embodiments, the Fc domain consists essentially of Pro100-Lys330 of Human IgG1. According to some embodiments, the Fc domain may be linked to rsNLGn4 through a linker. According to some embodiments, the linker may have the amino acid sequence set forth in SEQ ID NO: 13 (IEGRMD).

According to some embodiments, the agent is a chimeric protein formed from NLGn4 polypeptides or fragments fused with a second polypeptide to form a soluble NLGn4. According to some embodiments, the agent comprises a DNA sequences, which combine two partial DNA sequences, one sequence encoding soluble fragments of NLGn4 (i.e. the DNA sequence encoding the extracellular domain of NLGn4) and the other partial sequence encoding all domains except the first domain of the constant region of the heavy chain of human immunoglobulin IgG, IgA, IgM, or IgE. These DNA sequences may subsequently be expressed in target cells using expression vectors as known in the art, thereby obtaining endogenous expression of recombinant proteins having the extracellular domain of NLGn4 joined to the Fc fragment of an immunoglobulin molecule.

According to some embodiments, the NLGn4 is encoded by the sequence set forth in SEQ ID NO: 1.

According to some embodiments, the recombinant Nrx1b comprises A1a51-Ser363 of NP_620072. According to some embodiments, the recombinant Nrx1b consists essentially of Ala51-Ser363 of NP_620072.

According to some embodiments, the agent comprises recombinant soluble Nrx1b (rsNrx1b); wherein the rsNrx1b comprises the extracellular domain of Nrx1b or a fragment, derivative or analog thereof capable of binding NLGn4.

According to some embodiments, the extracellular domain of Nrx1b consists of SEQ ID NO: 10. According to some embodiments, the rsNrx1b consists of SEQ ID NO: 10, or a fragment, derivative or analog thereof.

According to some embodiments, the rsNrx1b competes with endogenous Nrx1b for binding to NLGn4.

According to some embodiments, the rsNrx1b is devoid of the intracellular domain and/or the transmembrane domain of Nrx1b.

According to some embodiments, Nrx1b is encoded by the sequence set forth in SEQ ID NO: 6.

According to some embodiments, the agent comprises a fusion protein comprising rsNrx1b and an immunoglobulin molecule. According to some embodiments, the agent comprises a fusion protein comprising rsNrx1b and an Fc domain of an immunoglobulin molecule, also referred to herein as rsNrx1b-Fc fusion protein. According to some embodiments, the Fc domain may include part or the entire CH1 domain, the CH2 domain, the CH3 domain and hinge region of IgG1, IgG2, IgG3 and IgG4. According to some embodiments, the Fc domain may be devoid of the CH1 domain. According to some embodiments, the Fc domain may include all domains of the Fc domain apart from CH1. According to some embodiments, the Fc domain comprises Pro100-Lys330 of Human IgG1. According to some embodiments, the Fc domain consists essentially of Pro100-Lys330 of Human IgG1. According to some embodiments, the Fc domain may be linked to rsNrx1b through a linker. According to some embodiments, the linker may have the amino acid sequence set forth in SEQ ID NO: 13 (IEGRMD).

According to some embodiments, the agent is a chimeric protein formed from Nrx1b polypeptides or fragments fused with a second polypeptide to form a soluble Nrx1. According to some embodiments, the agent comprises a DNA sequences, which combine two partial DNA sequences, one sequence encoding soluble fragments of Nrx1b (i.e. the DNA sequence encoding the extracellular domain of Nrx1b) and the other partial sequence encoding all domains except the first domain of the constant region of the heavy chain of human immunoglobulin IgG, IgA, IgM, or IgE. These DNA sequences may subsequently be expressed in target cells using expression vectors as known in the art, thereby obtaining endogenous expression of recombinant proteins having the extracellular domain of Nrx1b joined to the Fc fragment of an immunoglobulin molecule.

According to some embodiments, the agent comprises a combination of recombinant soluble NLGn4 and recombinant soluble Nrx1b (rsNrx1b).

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1: NLGn4 Gene is Over-Expressed in NASH Patients with Hepatic Fibrosis

Heparinized-blood samples of healthy volunteers and NAFLD patients and/or cirrhotic cases were obtained. Mononuclear cells were isolated by centrifugation over ficoll-hypaque (Pharmacia). After three washes in saline, cells were resuspended in medium of Roswell Park Memorial Institute 1640 with 10% FBS. Human NK cells were isolated from Peripheral blood lymphocytes (PBLs) using a magnetic cell sorting kit (Miltenyi Biotec) according to manufacturer's instructions. RNA was extracted, converted to cDNA and hybridized onto a spotted microarray.

Figure 2:
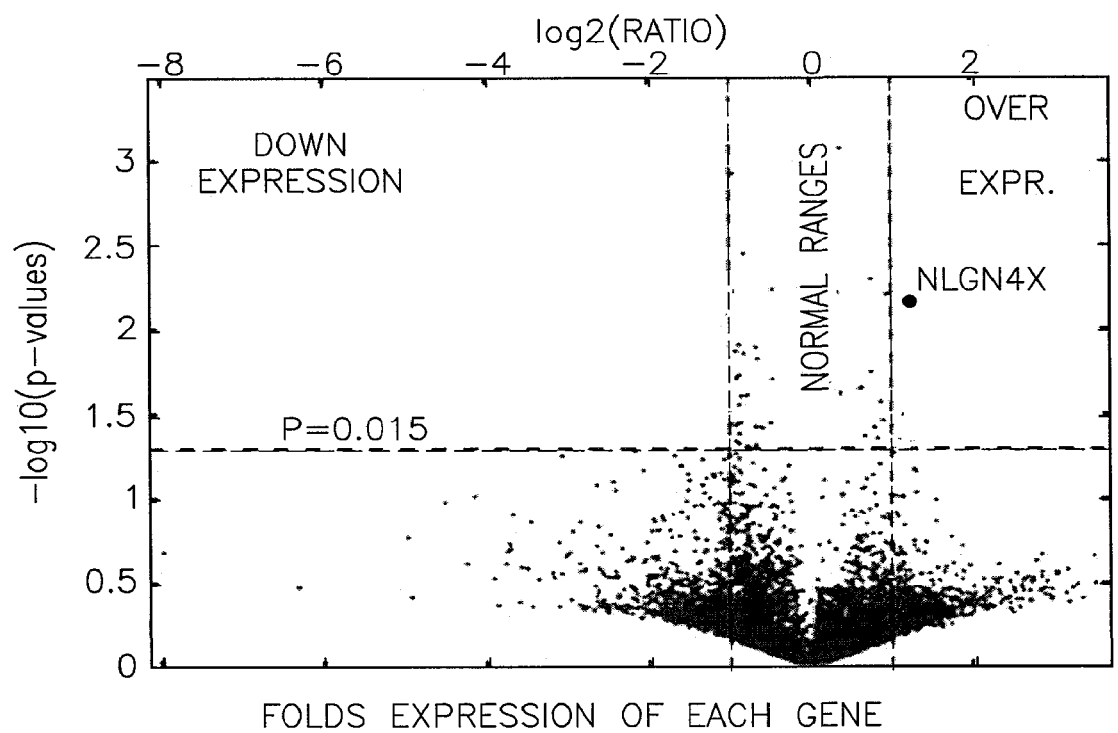
FIG. 2 shows NLGn4 expression in NK cells obtained from NASH patients with hepatic fibrosis. Isolated NK cells from healthy and NASH cirrhotic cases were assessed by DNA spotted Microarrays.

As seen in FIG. 2, a 4-fold increase in NLGn4 gene expression on NASH NK cells was obtained (in the zone of down- and up-expressed genes with a cutoff p-value of 0.015 showed), suggesting a correlation between NLGn4 expression levels and NAFLD/NASH in humans.

Figure 3:
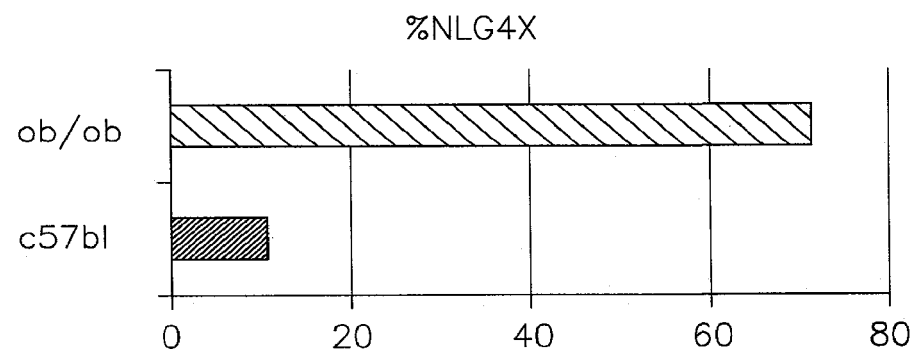
FIG. 3. Shows NLGn4 expression levels in a leptin-deficient fatty liver disease mouse model as compared control mice.

Example 2: Leptin-Deficient Mice (Ob/Ob) (Fatty Liver Disease Model) Show Increased NLGn4 Expression on Liver NK Cells RNA was extracted from Leptin deficient ob/ob mice (fatty liver disease mouse model), converted into cDNA and the expression level of NLGn4 analyzed by RT-PCR using NLGn4 specific primers. As seen in FIG. 3, the ob/ob mice showed a 4-fold increase in mRNA NLG4 expressions as compared to WT c57bl mice, serving as control. This result shows a correlation between NLGn4 overexpression and fatty liver disease in mice.

Figure 4A:
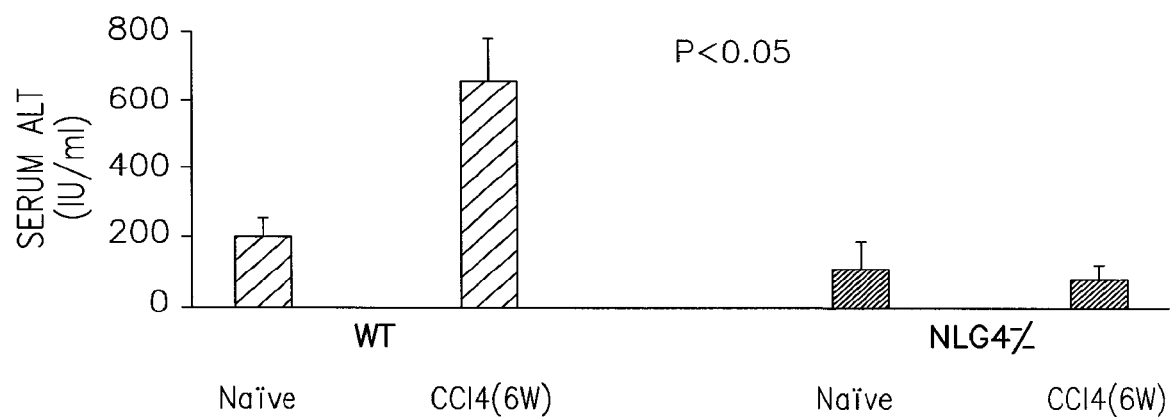
FIG. 4A shows serum ALT levels in homozygous NLG4−/− mice as compared to WT, upon induction of fibrosis.
Figure 4B:
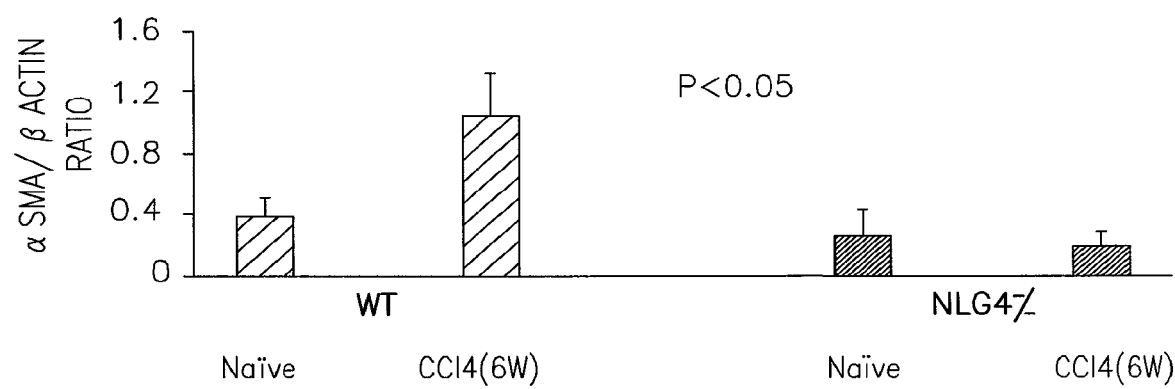
FIG. 4B shows alpha-SMA levels in homozygous NLG4−/− mice as compared to WT, upon induction of fibrosis.

Example 3: Homozygous NLG4-/- (KO) Mice Show Decreased Inflammation and Fibrosis Naïve Wild Type (WT) and homozygote NLG4-/- mice were induced for fibrosis by i.p injections of carbon tetrachloride 2x/week for 6 weeks and evaluated for serum levels of Alanine transaminase (ALT—biomarker for liver health). As seen from FIG. 4A, induction of fibrosis, by carbon tetrachloride injection, was significantly attenuated in the NLG4-/- KO mice as compared to WT. Furthermore, as shown in FIG. 4B, alpha-SMA (marker of HSC activation) levels were lower in the NLG4-/- mice compared to WT, as evaluated by quantitative western blot analysis.

These results show the involvement of NLGn4 in HSC activity and in the induction of fibrosis.

Example 4: Incubation of NK Cells with Anti-NLGn4 Antibodies Increases NK Cell Activation and Reduces HSC Activation in an In-Vitro Assay NK cells were isolated form peripheral blood derived from NAFLD patients with advanced fibrosis scoring (histology documentation of F3, F4). Patients without medications and lacking full metabolic syndrome were included. Isolated NK cells were incubated with 4, 8, 10 or 12 μM of anti-NLG4 (human NLGN4 Antibody, Antigen Affinity-purified Polyclonal Sheep IgG, R&D Systems Catalog #AF5158) for 3 hours prior to incubation with the myofibroblasts LX2-cell line (HSCs) o left untreated (0). Following 24 hours of NK-LX2 co-culture, harvested cells were analyzed by flow-cytometry for NK NLG4 and CD107a expressions as well as LX2 alpha-SMA intensity.

Figure 5A:
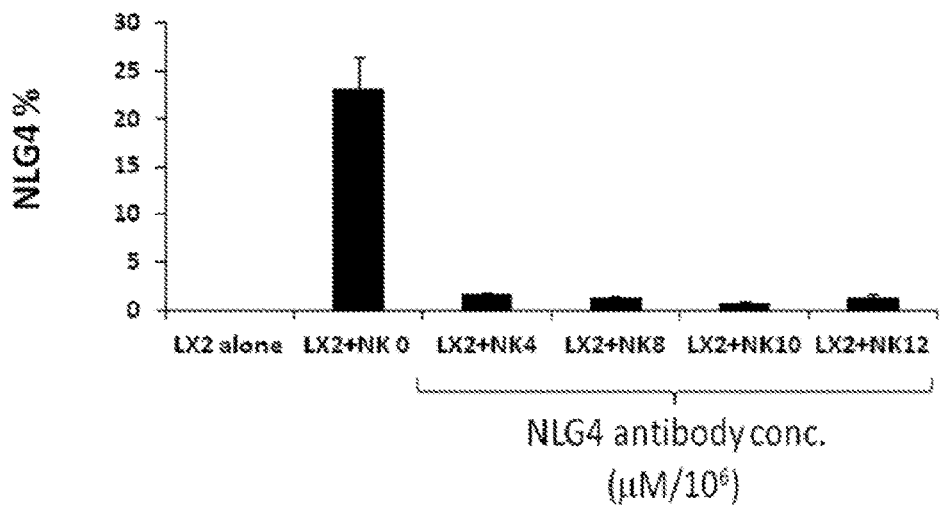
FIG. 5A shows NLGn4 protein expression levels in NK cells isolated from NAFLD patients and incubated with a hepatic stellate cell line (LX2) in the absence or in the presence of increasing concentrations of an anti-NLGn4 antibody.
Figure 5B:
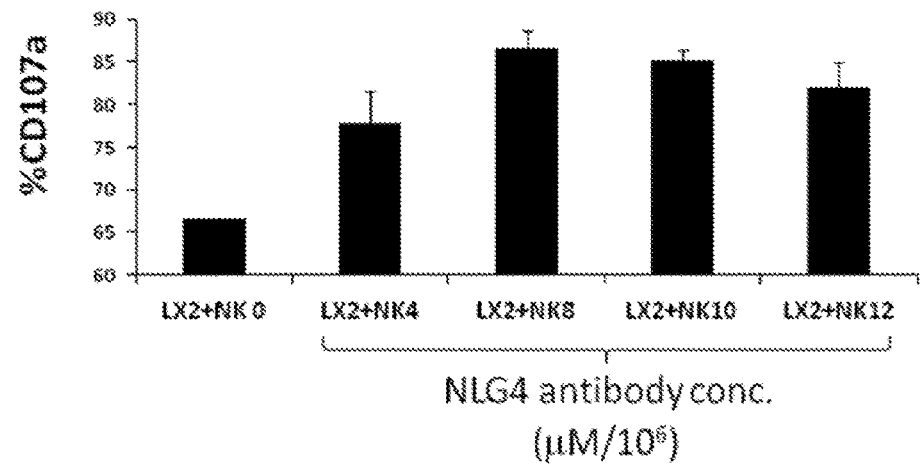
FIG. 5B shows CD107a levels in NK cells isolated from NAFLD patients and incubated with a hepatic stellate cell line in the absence or in the presence of increasing concentrations of an anti-NLGn4 antibody.

Incubation of the NK cells with an anti-NLG4 antibody significantly inhibited NLGn4 protein levels (FIG. 5A, $P<0.03$) and increased CD107a expression on the NK cells (FIG. 5B, $P<0.01$) in all tested concentrations. These results show that incubation of NK cells with anti-NLGn4 antibodies increase NK cell activity in-vitro.

Figure 5C:
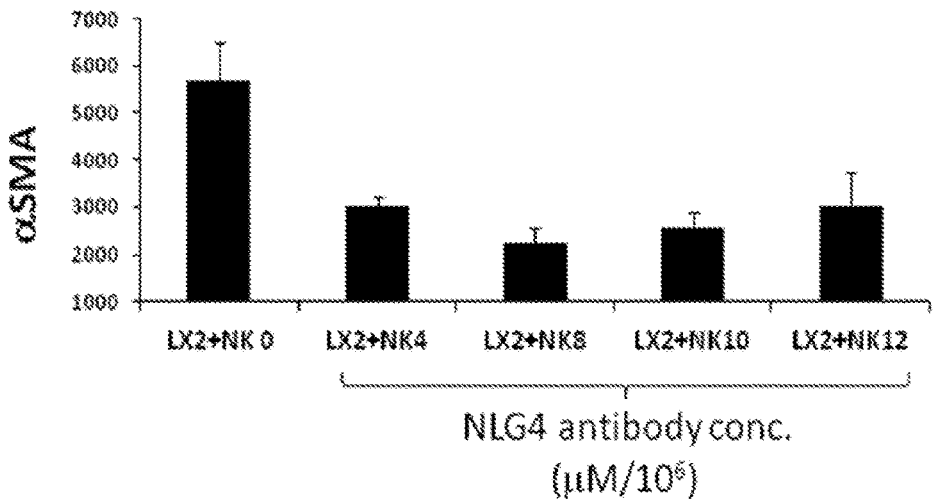
FIG. 5C shows alpha-SMA intensities (LX2 activity) in LX2 cells, incubated with NK cells isolated from NAFLD patients in the absence or in the presence of increasing concentrations of an anti-NLGn4 antibody.

The increased NK activity was accompanied with increased LX2 killing; as alpha-SMA mean fluorescence intensities decreased with the increase in anti-NLG4 concentrations (FIG. 5C, $P<0.01$). This shows that incubation of NK cells with anti-NLGn4 antibodies attenuates HSC activity in-vitro.

Example 5: Incubation with Anti-NLGn4 Antibodies Increases NK Cell Activation and Reduces HSC Activation in an In-Vivo Assay in Mice 25 WT naïve C57/BL mice (12 weeks) mice were either induced for acute hepatic fibrosis by i.p injections of carbon tetrachloride (3×/week) or left untreated (induced n=10, control n=10). One day after the last injection, the mice were either injected i.p. with NLGn4-antibodies (anti-human NLGN4 Antibody, Antigen Affinity-purified Polyclonal Sheep IgG, R&D Systems Catalog #AF5158) at concentrations of 82 mg/mice or left untreated (5 mice of each of the induced and control mice). 24 hours after injection with the NLGn4 antibodies, the mice were sacrificed and sera were collected for detection of CD107a expression (marker of NK activity), ALT levels biomarker for liver health and livers were harvested for assessment of alpha-SMA expression (marker of HSC activation) using an RT PCR assay.

Figure 6A:
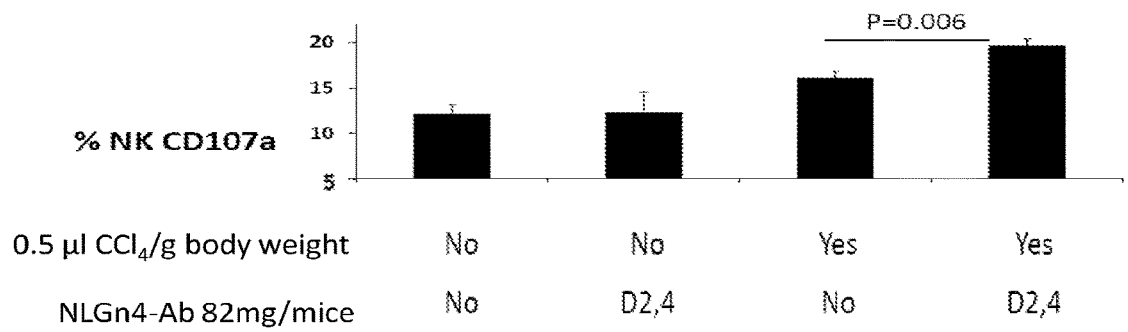
FIG. 6A shows CD107a levels in NK cells isolated from mice induced with carbon tetrachloride to cause acute hepatic fibrosis (or left untreated) and either injected with an anti-NLGn4 antibody or left untreated.
Figure 6B:
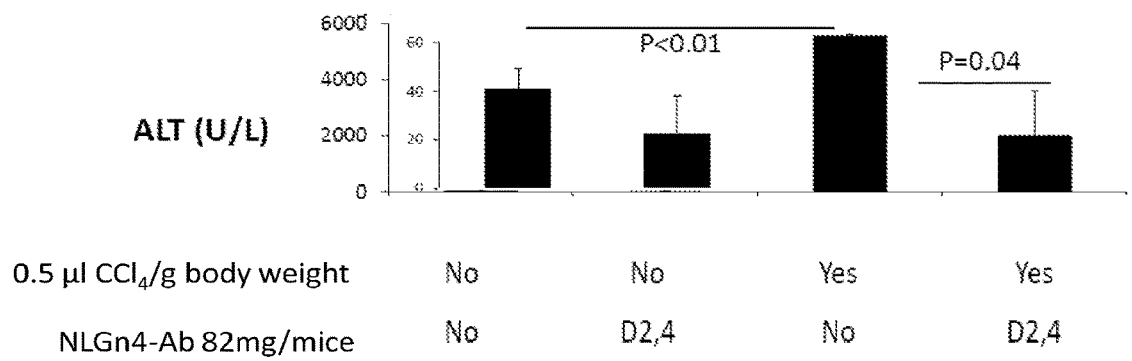
FIG. 6B shows serum ALT levels in WT mice induced with carbon tetrachloride to cause acute hepatic fibrosis (or left untreated) and either injected with an anti-NLGn4 antibody or left untreated.
Figure 6C:
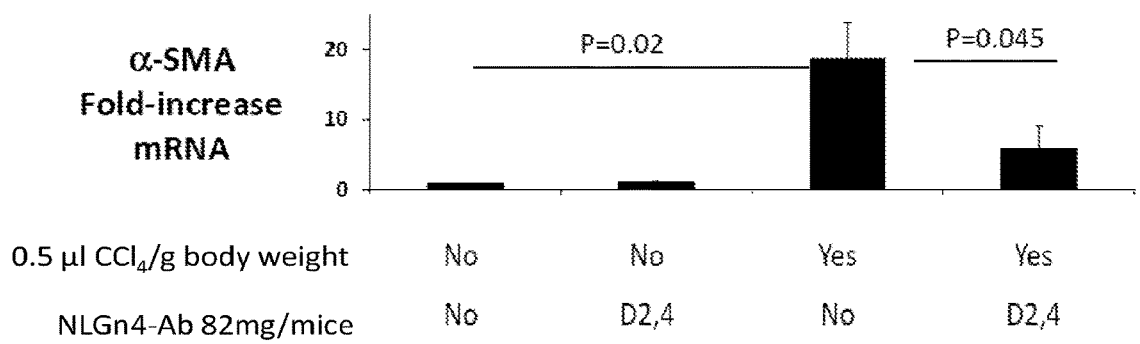
FIG. 6C shows alpha-SMA levels in WT mice induced with carbon tetrachloride to cause acute hepatic fibrosis (or left untreated) and either injected with an anti-NLGn4 antibody or left untreated.

As seen in FIG. 6A mice induced for acute liver fibrosis that were exposed to the NLGn4 antibody had increased CD107a expression (marker of NK activity), a lesser degree of liver injuries and fibrosis as evidenced by reduced serum ALT levels ($P=0.03$) (FIG. 6B) and alpha-SMC expression (FIG. 6C).

These results show that treatment with anti-NLGn4 antibodies reduces liver injuries and fibrosis in-vivo as well as in-vitro and show that anti-NLGn4 antibodies can serve as therapeutic agents in the treatment of liver disorders such as but not limited to NAFLD and for preventing progression to cirrhosis.

Figure 7:
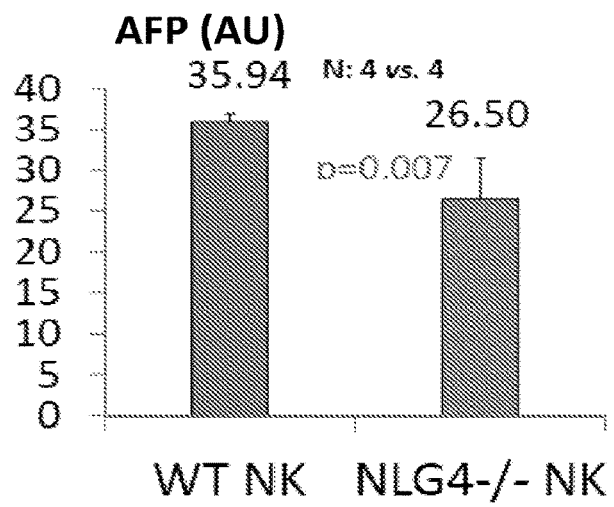
FIG. 7 shows α-feto-protein levels in mice induced for hepatocellular carcinoma by injection of human hepatoma cells (Hep3B) co-cultured with either wt or NLGn4−/− NK cells.

Example 6: Mice Induced for Hepatocellular Carcinoma by Injection of Human Hepatoma Cells (Hep3B) Co-Cultured with NLGn4-/- NK Cells Show Reduced Levels of the Cancer Marker α-Feto-Protein Human hepatoma cells (Hep3B) co-cultured for 24 h with either wt NK cells (n=4) or NLGn4-/- NK cells (n=4) were injected subcutaneously ($2\times10^6$) into C57Bl6 mice (13 week old). The mice were subsequently irradiated (5Gry) to induce tumor growth. Subsequently, plasma alpha-fetoprotein (AFP) levels were evaluated. AFP is a biomarker of liver cancers and levels above 500 nanograms/milliliter of AFP in adults is indicative of hepatocellular carcinoma, and metastatic cancers of the liver. As seen from FIG. 7, AFP levels were significantly lowered in mice injected with Hep3B cells incubated with NLG4-/- NK cells as compared to mice injected with Hep3B cells incubated with wt NK cells.

These results show the involvement of NLGn4 in NK cell attenuation and hepatoma formation and demonstrate that reducing NLGn4 protein levels inhibit tumor growth.

Example 7: Incubation of NK Cells with Recombinant Nrx1b Increases NK Cell Activation and Reduces HSC Activation in an In-Vitro Assay NK cells were isolated form peripheral blood derived from NAFLD patients with advanced fibrosis scoring (histology documentation of F3, F4). Patients without medications and lacking full metabolic syndrome were included. Isolated NK cells were incubated with 4 nM or 10 nM recombinant Nrx1b-Fc Chimera (Recombinant Human Neurexin 1β/NXRN1b Fc Chimera, R&D Systems Catalog Number: 5268-NX) including amino acids Ala51-Ser363 of Nrx1b (NP_620072) and Pro100-Lys330 of Human IgG1 linked by linker sequence IEGRMD, for 3 hours prior to the NK cells being co-cultured with the hepatic stellate cell line LX2. Following 24 hours of co-culture, harvested cells were analyzed by flow-cytometry for NK CD107a expression as well as LX2 alpha-SMA intensity.

Figure 8A:
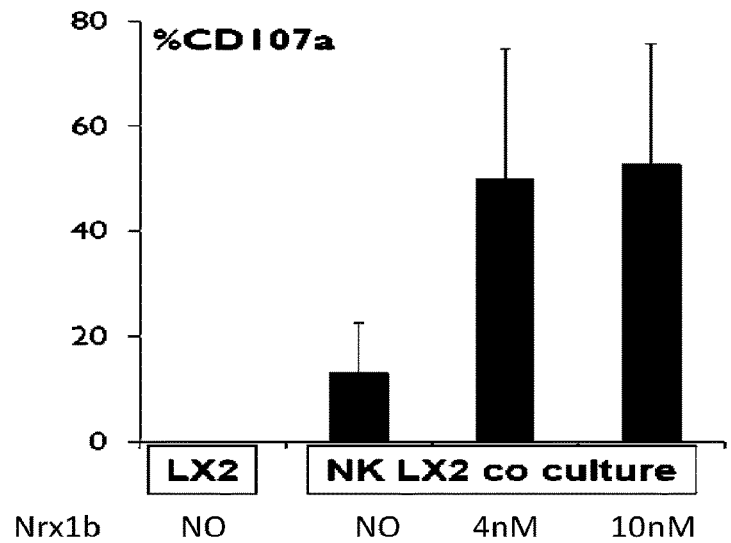
FIG. 8A shows CD107a levels in NK cells isolated from NAFLD patients and incubated with a hepatic stellate cell line in the absence or in the presence of recombinant Nrx1b (4 nM, 10 nM).

Incubation of the NK cells with recombinant Nrx1b significantly increased CD107a expression on the NK cells (FIG. 8A) at both concentrations. These results show that incubation of NK cells with recombinant Nrx1b increases NK cell activity in-vitro.

Figure 8B:
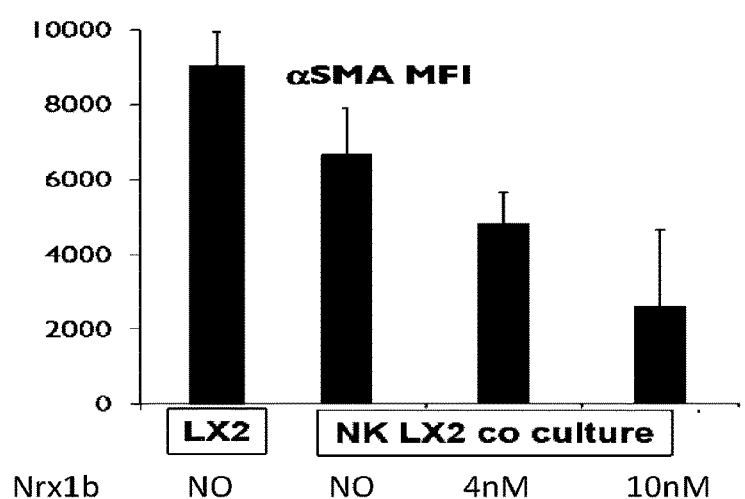
FIG. 8B shows alpha-SMA intensities (LX2 activity) in LX2 cells, incubated with NK cells isolated from NAFLD patients in the absence or in the presence of recombinant Nrx1b (4 nM, 10 nM).

The increased NK activity was accompanied with increased LX2 killing; as alpha-SMA mean fluorescence intensities decreased with the increase in Nrx1b concentrations (FIG. 8B). This shows that co-culturing HSC with NK cells pre-incubated with recombinant Nrx1b attenuate HSC activity in-vitro.

Example 8: Incubation with Recombinant Nrx1b Increases NK Cell Activation and Reduces HSC Activation in an In-Vivo Assay 25 WT naïve C57/BL mice (12 weeks) mice were either induced for acute hepatic fibrosis by i.p. injections of carbon tetrachloride (CC14-3×/week) or left untreated (induced n=12, control n=12). Either one day after the last injection (D9) or the day after each injection (D1, D3 and D7), the mice were injected i.p. with 0.2 µg recombinant Nrx1b/g body weight or left untreated (3 mice of each of the induced and control mice). 24 hours after the last injection with the recombinant Nrx1b-Fc Chimera (Recombinant Human Neurexin 1β/NXRN1b Fc Chimera, R&D Systems Catalog Number: 5268-NX) including amino acids Ala51-Ser363 of Nrx1b (NP_620072) and Pro100-Lys330 of Human IgG1 linked by linker sequence IEGRMD, the mice were sacrificed and sera were collected for detection of ALT levels and livers were harvested for assessment of alpha-SMA expression using an RT PCR assay.

Figure 9A:
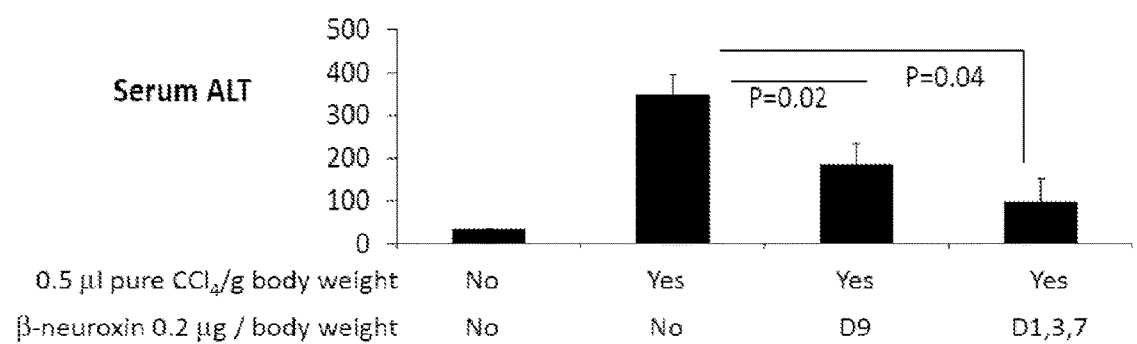
FIG. 9A shows serum ALT levels in WT mice induced with carbon tetrachloride to cause acute hepatic fibrosis (or left untreated) and either injected with a recombinant Nrx1b or left untreated.
Figure 9B:
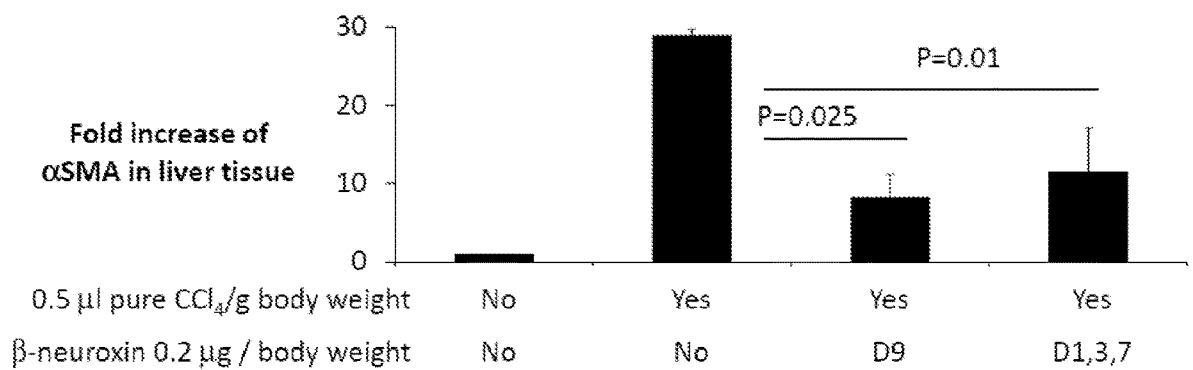
FIG. 9B shows alpha-SMA levels in WT mice induced with carbon tetrachloride to cause acute hepatic fibrosis (or left untreated) and either injected with recombinant Nrx1b or left untreated.

As seen in FIGS. 9A and 9B mice induced for acute liver fibrosis that were exposed to the recombinant Nrx1b had a lesser degree of liver injuries and fibrosis as evidenced by reduced serum ALT levels (FIG. 9A) and reduced alpha-SMC expression (FIG. 9B).

These results show that treatment with recombinant Nrx1b reduces liver injuries and fibrosis in-vivo as well as in-vitro and show that recombinant Nrx1b can serve as therapeutic agents in the treatment of liver disorders such as but not limited to NAFLD and for preventing progression to cirrhosis.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating, attenuating and/or preventing progression of a liver disorder, the method comprising administering a therapeutically effective amount of a recombinant soluble Nrx1b (rsNrx1b) comprising the extracellular domain of Nrx1b, capable of interfering with, inhibiting and/or preventing neuroligin 4 (NLGn4) Neurexin 113 (Nrx1b) protein-protein interaction; and a pharmaceutically acceptable carrier, thereby treating, attenuating and/or preventing the progression of the liver disorder.

2. The method of claim 1, wherein the extracellular domain of Nrx1b consists of SEQ ID NO: 10.

3. The method of claim 1, wherein the rsNrx1b consists of SEQ ID NO: 10.

4. The method of claim 1, wherein the rsNrx1b competes with endogenous Nrx1b for binding to NLGn4.

5. The method of claim 1, wherein the rsNrx1b is devoid of the intracellular domain and/or the transmembrane domain of Nrx1b.

6. The method of claim 1, wherein the rsNrx1b is fused to Fc portion of an immunoglobulin molecule to form a fusion protein.

7. The method of claim 6, wherein the fusion protein comprises the Fc portion of the immunoglobulin molecule fused to a peptide having an amino acid sequence as set forth in SEQ ID NO: 10.

8. The method of claim 1, wherein NLGn4 is encoded by the sequence set forth in SEQ ID NO: 1.

9. The method of claim 1, wherein Nrx1b is encoded by the sequence set forth in SEQ ID NO: 6.

10. The method of claim 1, wherein the liver disorder comprises fibrosis.

11. The method of claim 1, wherein the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof.

12. The method of claim 11, wherein the liver disorder is NAFLD.

13. The method of claim 11, wherein the liver disorder is hepatocellular carcinoma.

* * * * *

SEQUENCE LISTING

```
<160> NUMBER OF SEQ ID NOS: 13

<210> SEQ ID NO 1
<211> LENGTH: 816
<212> TYPE: PRT
<213> ORGANISM: Homo sapiens

<400> SEQUENCE: 1

Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
                20                  25                  30

Ala Ile Lys Phe Thr Leu Ile Asp Ser Gln Ala Gln Tyr Pro Val Val
                35                  40                  45

Asn Thr Asn Tyr Gly Lys Ile Arg Gly Leu Arg Thr Pro Leu Pro Asn
            50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Pro Pro Ser Ser
                85                  90                  95

Trp Thr Gly Ile Arg Asn Thr Thr Gln Phe Ala Ala Val Cys Pro Gln
                100                 105                 110

His Leu Asp Glu Arg Ser Leu Leu His Asp Met Leu Pro Ile Trp Phe
            115                 120                 125

Thr Ala Asn Leu Asp Thr Leu Met Thr Tyr Val Gln Asp Gln Asn Glu
        130                 135                 140

Asp Cys Leu Tyr Leu Asn Ile Tyr Val Pro Thr Glu Asp Asp Ile His
145                 150                 155                 160

Asp Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser
                180                 185                 190

Tyr Gly Asn Val Ile Val Ile Thr Ile Asn Tyr Arg Leu Gly Ile Leu
            195                 200                 205

Gly Phe Leu Ser Thr Gly Asp Gln Ala Ala Lys Gly Asn Tyr Gly Leu
        210                 215                 220

Leu Asp Gln Ile Gln Ala Leu Arg Trp Ile Glu Glu Asn Val Gly Ala
225                 230                 235                 240

Phe Gly Gly Asp Pro Lys Arg Val Thr Ile Phe Gly Ser Gly Ala Gly
                245                 250                 255

Ala Ser Cys Val Ser Leu Leu Thr Leu Ser His Tyr Ser Glu Gly Leu
                260                 265                 270

Phe Gln Lys Ala Ile Ile Gln Ser Gly Thr Ala Leu Ser Ser Trp Ala
            275                 280                 285

Val Asn Tyr Gln Pro Ala Lys Tyr Thr Arg Ile Leu Ala Asp Lys Val
        290                 295                 300
```

```
Gly Cys Asn Met Leu Asp Thr Thr Asp Met Val Glu Cys Leu Arg Asn
305                 310                 315                 320

Lys Asn Tyr Lys Glu Leu Ile Gln Gln Thr Ile Thr Pro Ala Thr Tyr
            325                 330                 335

His Ile Ala Phe Gly Pro Val Ile Asp Gly Asp Val Ile Pro Asp Asp
                340                 345                 350

Pro Gln Ile Leu Met Glu Gln Gly Glu Phe Leu Asn Tyr Asp Ile Met
            355                 360                 365

Leu Gly Val Asn Gln Gly Gly Leu Lys Phe Val Asp Gly Ile Val
    370                 375                 380

Asp Asn Glu Asp Gly Val Thr Pro Asn Asp Phe Asp Phe Ser Val Ser
385                 390                 395                 400

Asn Phe Val Asp Asn Leu Tyr Gly Tyr Pro Glu Gly Lys Asp Thr Leu
                405                 410                 415

Arg Glu Thr Ile Lys Phe Met Tyr Thr Asp Trp Ala Asp Lys Glu Asn
                420                 425                 430

Pro Glu Thr Arg Arg Lys Thr Leu Val Ala Leu Phe Thr Asp His Gln
            435                 440                 445

Trp Val Ala Pro Ala Val Ala Thr Ala Asp Leu His Ala Gln Tyr Gly
    450                 455                 460

Ser Pro Thr Tyr Phe Tyr Ala Phe Tyr His His Cys Gln Ser Glu Met
465                 470                 475                 480

Lys Pro Ser Trp Ala Asp Ser Ala His Gly Asp Glu Val Pro Tyr Val
                485                 490                 495

Phe Gly Ile Pro Met Ile Gly Pro Thr Glu Leu Phe Ser Cys Asn Phe
                500                 505                 510

Ser Lys Asn Asp Val Met Leu Ser Ala Val Val Met Thr Tyr Trp Thr
    515                 520                 525

Asn Phe Ala Lys Thr Gly Asp Pro Asn Gln Pro Val Pro Gln Asp Thr
    530                 535                 540

Lys Phe Ile His Thr Lys Pro Asn Arg Phe Glu Glu Val Ala Trp Ser
545                 550                 555                 560

Lys Tyr Asn Pro Lys Asp Gln Leu Tyr Leu His Ile Gly Leu Lys Pro
                565                 570                 575

Arg Val Arg Asp His Tyr Arg Ala Thr Lys Val Ala Phe Trp Leu Glu
            580                 585                 590

Leu Val Pro His Leu His Asn Leu Asn Glu Ile Phe Gln Tyr Val Ser
            595                 600                 605

Thr Thr Thr Lys Val Pro Pro Pro Asp Met Thr Ser Phe Pro Tyr Gly
    610                 615                 620

Thr Arg Arg Ser Pro Ala Lys Ile Trp Pro Thr Thr Lys Arg Pro Ala
625                 630                 635                 640

Ile Thr Pro Ala Asn Asn Pro Lys His Ser Lys Asp Pro His Lys Thr
                645                 650                 655

Gly Pro Glu Asp Thr Thr Val Leu Ile Glu Thr Lys Asp Tyr Ser
            660                 665                 670

Thr Glu Leu Ser Val Thr Ile Ala Val Gly Ala Ser Leu Leu Phe Leu
            675                 680                 685

Asn Ile Leu Ala Phe Ala Ala Leu Tyr Tyr Lys Lys Asp Lys Arg Arg
    690                 695                 700

His Glu Thr His Arg Arg Pro Ser Pro Gln Arg Asn Thr Thr Asn Asp
705                 710                 715                 720

Ile Ala His Ile Gln Asn Glu Glu Ile Met Ser Leu Gln Met Lys Gln
```

-continued

```
                725                 730                 735

Leu Glu His Asp His Glu Cys Glu Ser Leu Gln Ala His Asp Thr Leu
            740                 745                 750

Arg Leu Thr Cys Pro Pro Asp Tyr Thr Leu Thr Leu Arg Arg Ser Pro
        755                 760                 765

Asp Asp Ile Pro Leu Met Thr Pro Asn Thr Ile Thr Met Ile Pro Asn
    770                 775                 780

Thr Leu Thr Gly Met Gln Pro Leu His Thr Phe Asn Thr Phe Ser Gly
785                 790                 795                 800

Gly Gln Asn Ser Thr Asn Leu Pro His Gly His Ser Thr Thr Arg Val
                805                 810                 815

<210> SEQ ID NO 2
<211> LENGTH: 6
<212> TYPE: PRT
<213> ORGANISM: Artificial Sequence
<220> FEATURE:
<223> OTHER INFORMATION: peptide

<400> SEQUENCE: 2

Gln Gly Glu Phe Leu Asn
1               5

<210> SEQ ID NO 3
<211> LENGTH: 10
<212> TYPE: PRT
<213> ORGANISM: Artificial Sequence
<220> FEATURE:
<223> OTHER INFORMATION: peptide

<400> SEQUENCE: 3

Ser Leu Leu Thr Leu Ser His Tyr Ser Glu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: peptide

<400> SEQUENCE: 4

Ala Gln Tyr Gly Ser Pro Thr Tyr Phe Tyr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: peptide

<400> SEQUENCE: 5

Leu Ser His Tyr Ser Glu Gly Leu Phe Gln Lys
1               5                   10

<210> SEQ ID NO 6
<211> LENGTH: 1547
<212> TYPE: PRT
<213> ORGANISM: Homo sapiens

<400> SEQUENCE: 6

Met Gly Thr Ala Leu Leu Gln Arg Gly Gly Cys Phe Leu Leu Cys Leu
1               5                   10                  15
```

```
Ser Leu Leu Leu Leu Gly Cys Trp Ala Glu Leu Gly Ser Gly Leu Glu
            20                  25                  30

Phe Pro Gly Ala Glu Gly Gln Trp Thr Arg Phe Pro Lys Trp Asn Ala
        35                  40                  45

Cys Cys Glu Ser Glu Met Ser Phe Gln Leu Lys Thr Arg Ser Ala Arg
 50                  55                  60

Gly Leu Val Leu Tyr Phe Asp Asp Glu Gly Phe Cys Asp Phe Leu Glu
 65                  70                  75                  80

Leu Ile Leu Thr Arg Gly Gly Arg Leu Gln Leu Ser Phe Ser Ile Phe
            85                  90                  95

Cys Ala Glu Pro Ala Thr Leu Leu Ala Asp Thr Pro Val Asn Asp Gly
            100                 105                 110

Ala Trp His Ser Val Arg Ile Arg Arg Gln Phe Arg Asn Thr Thr Leu
            115                 120                 125

Phe Ile Asp Gln Val Glu Ala Lys Trp Val Glu Val Lys Ser Lys Arg
        130                 135                 140

Arg Asp Met Thr Val Phe Ser Gly Leu Phe Val Gly Gly Leu Pro Pro
145                 150                 155                 160

Glu Leu Arg Ala Ala Leu Lys Leu Thr Leu Ala Ser Val Arg Glu
            165                 170                 175

Arg Glu Pro Phe Lys Gly Trp Ile Arg Asp Val Arg Val Asn Ser Ser
            180                 185                 190

Gln Val Leu Pro Val Asp Ser Gly Glu Val Lys Leu Asp Asp Glu Pro
        195                 200                 205

Pro Asn Ser Gly Gly Gly Ser Pro Cys Glu Ala Gly Glu Glu Gly Glu
        210                 215                 220

Gly Gly Val Cys Leu Asn Gly Gly Val Cys Ser Val Val Asp Asp Gln
225                 230                 235                 240

Ala Val Cys Asp Cys Ser Arg Thr Gly Phe Arg Gly Lys Asp Cys Ser
            245                 250                 255

Gln Glu Ile Lys Phe Gly Leu Gln Cys Val Leu Pro Val Leu Leu His
            260                 265                 270

Asp Asn Asp Gln Gly Lys Tyr Cys Cys Ile Asn Thr Ala Lys Pro Leu
        275                 280                 285

Thr Glu Lys Asp Asn Asn Val Glu Gly Leu Ala His Leu Met Met Gly
        290                 295                 300

Asp Gln Gly Lys Ser Lys Gly Lys Glu Glu Tyr Ile Ala Thr Phe Lys
305                 310                 315                 320

Gly Ser Glu Tyr Phe Cys Tyr Asp Leu Ser Gln Asn Pro Ile Gln Ser
            325                 330                 335

Ser Ser Asp Glu Ile Thr Leu Ser Phe Lys Thr Leu Gln Arg Asn Gly
        340                 345                 350

Leu Met Leu His Thr Gly Lys Ser Ala Asp Tyr Val Asn Leu Ala Leu
        355                 360                 365

Lys Asn Gly Ala Val Ser Leu Val Ile Asn Leu Gly Ser Gly Ala Phe
        370                 375                 380

Glu Ala Leu Val Glu Pro Val Asn Gly Lys Phe Asn Asp Asn Ala Trp
385                 390                 395                 400

His Asp Val Lys Val Thr Arg Asn Leu Arg Gln His Ser Gly Ile Gly
            405                 410                 415

His Ala Met Val Asn Lys Leu His Cys Ser Val Thr Ile Ser Val Asp
            420                 425                 430
```

```
Gly Ile Leu Thr Thr Thr Gly Tyr Thr Gln Asp Tyr Thr Met Leu
            435                 440                 445

Gly Ser Asp Asp Phe Phe Tyr Val Gly Gly Ser Pro Ser Thr Ala Asp
450                 455                 460

Leu Pro Gly Ser Pro Val Ser Asn Asn Phe Met Gly Cys Leu Lys Glu
465                 470                 475                 480

Val Val Tyr Lys Asn Asn Asp Val Arg Leu Glu Leu Ser Arg Leu Ala
                485                 490                 495

Lys Gln Gly Asp Pro Lys Met Lys Ile His Gly Val Val Ala Phe Lys
                500                 505                 510

Cys Glu Asn Val Ala Thr Leu Asp Pro Ile Thr Phe Glu Thr Pro Glu
                515                 520                 525

Ser Phe Ile Ser Leu Pro Lys Trp Asn Ala Lys Lys Thr Gly Ser Ile
                530                 535                 540

Ser Phe Asp Phe Arg Thr Thr Glu Pro Asn Gly Leu Ile Leu Phe Ser
545                 550                 555                 560

His Gly Lys Pro Arg His Gln Lys Asp Ala Lys His Pro Gln Met Ile
                565                 570                 575

Lys Val Asp Phe Phe Ala Ile Glu Met Leu Asp Gly His Leu Tyr Leu
                580                 585                 590

Leu Leu Asp Met Gly Ser Gly Thr Ile Lys Ile Lys Ala Leu Leu Lys
                595                 600                 605

Lys Val Asn Asp Gly Glu Trp Tyr His Val Asp Phe Gln Arg Asp Gly
                610                 615                 620

Arg Ser Gly Thr Ile Ser Val Asn Thr Leu Arg Thr Pro Tyr Thr Ala
625                 630                 635                 640

Pro Gly Glu Ser Glu Ile Leu Asp Leu Asp Asp Glu Leu Tyr Leu Gly
                645                 650                 655

Gly Leu Pro Glu Asn Lys Ala Gly Leu Val Phe Pro Thr Glu Val Trp
                660                 665                 670

Thr Ala Leu Leu Asn Tyr Gly Tyr Val Gly Cys Ile Arg Asp Leu Phe
                675                 680                 685

Ile Asp Gly Gln Ser Lys Asp Ile Arg Gln Met Ala Glu Val Gln Ser
                690                 695                 700

Thr Ala Gly Val Lys Pro Ser Cys Ser Lys Glu Thr Ala Lys Pro Cys
705                 710                 715                 720

Leu Ser Asn Pro Cys Lys Asn Asn Gly Met Cys Arg Asp Gly Trp Asn
                725                 730                 735

Arg Tyr Val Cys Asp Cys Ser Gly Thr Gly Tyr Leu Gly Arg Ser Cys
                740                 745                 750

Glu Arg Glu Ala Thr Val Leu Ser Tyr Asp Gly Ser Met Phe Met Lys
                755                 760                 765

Ile Gln Leu Pro Val Val Met His Thr Glu Ala Glu Asp Val Ser Leu
                770                 775                 780

Arg Phe Arg Ser Gln Arg Ala Tyr Gly Ile Leu Met Ala Thr Thr Ser
785                 790                 795                 800

Arg Asp Ser Ala Asp Thr Leu Arg Leu Glu Leu Asp Ala Gly Arg Val
                805                 810                 815

Lys Leu Thr Val Asn Leu Asp Cys Ile Arg Ile Asn Cys Asn Ser Ser
                820                 825                 830

Lys Gly Pro Glu Thr Leu Phe Ala Gly Tyr Asn Leu Asn Asp Asn Glu
                835                 840                 845

Trp His Thr Val Arg Val Val Arg Arg Gly Lys Ser Leu Lys Leu Thr
```

```
            850             855             860
Val Asp Asp Gln Gln Ala Met Thr Gly Gln Met Ala Gly Asp His Thr
865             870             875             880

Arg Leu Glu Phe His Asn Ile Glu Thr Gly Ile Ile Thr Glu Arg Arg
                885             890             895

Tyr Leu Ser Ser Val Pro Ser Asn Phe Ile Gly His Leu Gln Ser Leu
            900             905             910

Thr Phe Asn Gly Met Ala Tyr Ile Asp Leu Cys Lys Asn Gly Asp Ile
        915             920             925

Asp Tyr Cys Glu Leu Asn Ala Arg Phe Gly Phe Arg Asn Ile Ile Ala
    930             935             940

Asp Pro Val Thr Phe Lys Thr Lys Ser Ser Tyr Val Ala Leu Ala Thr
945             950             955             960

Leu Gln Ala Tyr Thr Ser Met His Leu Phe Gln Phe Lys Thr Thr
                965             970             975

Ser Leu Asp Gly Leu Ile Leu Tyr Asn Ser Gly Asp Gly Asn Asp Phe
            980             985             990

Ile Val Val Glu Leu Val Lys Gly Tyr Leu His Tyr Val Phe Asp Leu
        995             1000            1005

Gly Asn Gly Ala Asn Leu Ile Lys Gly Ser Ser Asn Lys Pro Leu
    1010            1015            1020

Asn Asp Asn Gln Trp His Asn Val Met Ile Ser Arg Asp Thr Ser
    1025            1030            1035

Asn Leu His Thr Val Lys Ile Asp Thr Lys Ile Thr Thr Gln Ile
    1040            1045            1050

Thr Ala Gly Ala Arg Asn Leu Asp Leu Lys Ser Asp Leu Tyr Ile
    1055            1060            1065

Gly Gly Val Ala Lys Glu Thr Tyr Lys Ser Leu Pro Lys Leu Val
    1070            1075            1080

His Ala Lys Glu Gly Phe Gln Gly Cys Leu Ala Ser Val Asp Leu
    1085            1090            1095

Asn Gly Arg Leu Pro Asp Leu Ile Ser Asp Ala Leu Phe Cys Asn
    1100            1105            1110

Gly Gln Ile Glu Arg Gly Cys Glu Gly Pro Ser Thr Thr Cys Gln
    1115            1120            1125

Glu Asp Ser Cys Ser Asn Gln Gly Val Cys Leu Gln Gln Trp Asp
    1130            1135            1140

Gly Phe Ser Cys Asp Cys Ser Met Thr Ser Phe Ser Gly Pro Leu
    1145            1150            1155

Cys Asn Asp Pro Gly Thr Thr Tyr Ile Phe Ser Lys Gly Gly Gly
    1160            1165            1170

Gln Ile Thr Tyr Lys Trp Pro Pro Asn Asp Arg Pro Ser Thr Arg
    1175            1180            1185

Ala Asp Arg Leu Ala Ile Gly Phe Ser Thr Val Gln Lys Glu Ala
    1190            1195            1200

Val Leu Val Arg Val Asp Ser Ser Ser Gly Leu Gly Asp Tyr Leu
    1205            1210            1215

Glu Leu His Ile His Gln Gly Lys Ile Gly Val Lys Phe Asn Val
    1220            1225            1230

Gly Thr Asp Asp Ile Ala Ile Glu Glu Ser Asn Ala Ile Ile Asn
    1235            1240            1245

Asp Gly Lys Tyr His Val Val Arg Phe Thr Arg Ser Gly Gly Asn
    1250            1255            1260
```

Ala Thr Leu Gln Val Asp Ser Trp Pro Val Ile Glu Arg Tyr Pro
        1265                1270                1275

Ala Gly Asn Asn Asp Asn Glu Arg Leu Ala Ile Ala Arg Gln Arg
        1280                1285                1290

Ile Pro Tyr Arg Leu Gly Arg Val Val Asp Glu Trp Leu Leu Asp
        1295                1300                1305

Lys Gly Arg Gln Leu Thr Ile Phe Asn Ser Gln Ala Thr Ile Ile
        1310                1315                1320

Ile Gly Gly Lys Glu Gln Gly Gln Pro Phe Gln Gly Gln Leu Ser
        1325                1330                1335

Gly Leu Tyr Tyr Asn Gly Leu Lys Val Leu Asn Met Ala Ala Glu
        1340                1345                1350

Asn Asp Ala Asn Ile Ala Ile Val Gly Asn Val Arg Leu Val Gly
        1355                1360                1365

Glu Val Pro Ser Ser Met Thr Thr Glu Ser Thr Ala Thr Ala Met
        1370                1375                1380

Gln Ser Glu Met Ser Thr Ser Ile Met Glu Thr Thr Thr Thr Leu
        1385                1390                1395

Ala Thr Ser Thr Ala Arg Arg Gly Lys Pro Pro Thr Lys Glu Pro
        1400                1405                1410

Ile Ser Gln Thr Thr Asp Asp Ile Leu Val Ala Ser Ala Glu Cys
        1415                1420                1425

Pro Ser Asp Asp Glu Asp Ile Asp Pro Cys Glu Pro Ser Ser Gly
        1430                1435                1440

Gly Leu Ala Asn Pro Thr Arg Ala Gly Gly Arg Glu Pro Tyr Pro
        1445                1450                1455

Gly Ser Ala Glu Val Ile Arg Glu Ser Ser Ser Thr Thr Gly Met
        1460                1465                1470

Val Val Gly Ile Val Ala Ala Ala Ala Leu Cys Ile Leu Ile Leu
        1475                1480                1485

Leu Tyr Ala Met Tyr Lys Tyr Arg Asn Arg Asp Glu Gly Ser Tyr
        1490                1495                1500

His Val Asp Glu Ser Arg Asn Tyr Ile Ser Asn Ser Ala Gln Ser
        1505                1510                1515

Asn Gly Ala Val Val Lys Glu Lys Gln Pro Ser Ser Ala Lys Ser
        1520                1525                1530

Ser Asn Lys Asn Lys Lys Asn Lys Asp Lys Glu Tyr Tyr Val
        1535                1540                1545

<210> SEQ ID NO 7
<211> LENGTH: 635
<212> TYPE: PRT
<213> ORGANISM: Artificial Sequence
<220> FEATURE:
<223> OTHER INFORMATION: NLGn4 extracellular domain

<400> SEQUENCE: 7

Gln Ala Gln Tyr Pro Val Val Asn Thr Asn Tyr Gly Lys Ile Arg Gly
1               5                   10                  15

Leu Arg Thr Pro Leu Pro Asn Glu Ile Leu Gly Pro Val Glu Gln Tyr
            20                  25                  30

Leu Gly Val Pro Tyr Ala Ser Pro Pro Thr Gly Glu Arg Arg Phe Gln
        35                  40                  45

Pro Pro Glu Pro Pro Ser Ser Trp Thr Gly Ile Arg Asn Thr Thr Gln
    50                  55                  60

```
Phe Ala Ala Val Cys Pro Gln His Leu Asp Glu Arg Ser Leu Leu His
 65                  70                  75                  80

Asp Met Leu Pro Ile Trp Phe Thr Ala Asn Leu Asp Thr Leu Met Thr
                 85                  90                  95

Tyr Val Gln Asp Gln Asn Glu Asp Cys Leu Tyr Leu Asn Ile Tyr Val
            100                 105                 110

Pro Thr Glu Asp Asp Ile His Asp Gln Asn Ser Lys Lys Pro Val Met
        115                 120                 125

Val Tyr Ile His Gly Gly Ser Tyr Met Glu Gly Thr Gly Asn Met Ile
130                 135                 140

Asp Gly Ser Ile Leu Ala Ser Tyr Gly Asn Val Ile Val Ile Thr Ile
145                 150                 155                 160

Asn Tyr Arg Leu Gly Ile Leu Gly Phe Leu Ser Thr Gly Asp Gln Ala
                165                 170                 175

Ala Lys Gly Asn Tyr Gly Leu Leu Asp Gln Ile Gln Ala Leu Arg Trp
            180                 185                 190

Ile Glu Glu Asn Val Gly Ala Phe Gly Gly Asp Pro Lys Arg Val Thr
        195                 200                 205

Ile Phe Gly Ser Gly Ala Gly Ala Ser Cys Val Ser Leu Leu Thr Leu
210                 215                 220

Ser His Tyr Ser Glu Gly Leu Phe Gln Lys Ala Ile Ile Gln Ser Gly
225                 230                 235                 240

Thr Ala Leu Ser Ser Trp Ala Val Asn Tyr Gln Pro Ala Lys Tyr Thr
                245                 250                 255

Arg Ile Leu Ala Asp Lys Val Gly Cys Asn Met Leu Asp Thr Thr Asp
            260                 265                 270

Met Val Glu Cys Leu Arg Asn Lys Asn Tyr Lys Glu Leu Ile Gln Gln
        275                 280                 285

Thr Ile Thr Pro Ala Thr Tyr His Ile Ala Phe Gly Pro Val Ile Asp
290                 295                 300

Gly Asp Val Ile Pro Asp Pro Gln Ile Leu Met Glu Gln Gly Glu
305                 310                 315                 320

Phe Leu Asn Tyr Asp Ile Met Leu Gly Val Asn Gln Gly Glu Gly Leu
                325                 330                 335

Lys Phe Val Asp Gly Ile Val Asp Asn Glu Asp Gly Val Thr Pro Asn
            340                 345                 350

Asp Phe Asp Phe Ser Val Ser Asn Phe Val Asp Asn Leu Tyr Gly Tyr
        355                 360                 365

Pro Glu Gly Lys Asp Thr Leu Arg Glu Thr Ile Lys Phe Met Tyr Thr
370                 375                 380

Asp Trp Ala Asp Lys Glu Asn Pro Glu Thr Arg Arg Lys Thr Leu Val
385                 390                 395                 400

Ala Leu Phe Thr Asp His Gln Trp Val Ala Pro Ala Val Ala Thr Ala
                405                 410                 415

Asp Leu His Ala Gln Tyr Gly Ser Pro Thr Tyr Phe Tyr Ala Phe Tyr
            420                 425                 430

His His Cys Gln Ser Glu Met Lys Pro Ser Trp Ala Asp Ser Ala His
        435                 440                 445

Gly Asp Glu Val Pro Tyr Val Phe Gly Ile Pro Met Ile Gly Pro Thr
450                 455                 460

Glu Leu Phe Ser Cys Asn Phe Ser Lys Asn Asp Val Met Leu Ser Ala
465                 470                 475                 480
```

```
Val Val Met Thr Tyr Trp Thr Asn Phe Ala Lys Thr Gly Asp Pro Asn
                485                 490                 495

Gln Pro Val Pro Gln Asp Thr Lys Phe Ile His Thr Lys Pro Asn Arg
        500                 505                 510

Phe Glu Glu Val Ala Trp Ser Lys Tyr Asn Pro Lys Asp Gln Leu Tyr
            515                 520                 525

Leu His Ile Gly Leu Lys Pro Arg Val Arg Asp His Tyr Arg Ala Thr
        530                 535                 540

Lys Val Ala Phe Trp Leu Glu Leu Val Pro His Leu His Asn Leu Asn
545                 550                 555                 560

Glu Ile Phe Gln Tyr Val Ser Thr Thr Thr Lys Val Pro Pro Pro Asp
                565                 570                 575

Met Thr Ser Phe Pro Tyr Gly Thr Arg Arg Ser Pro Ala Lys Ile Trp
            580                 585                 590

Pro Thr Thr Lys Arg Pro Ala Ile Thr Pro Ala Asn Asn Pro Lys His
            595                 600                 605

Ser Lys Asp Pro His Lys Thr Gly Pro Glu Asp Thr Thr Val Leu Ile
        610                 615                 620

Glu Thr Lys Arg Asp Tyr Ser Thr Glu Leu Ser
625                 630                 635

<210> SEQ ID NO 8
<211> LENGTH: 119
<212> TYPE: PRT
<213> ORGANISM: Artificial Sequence
<220> FEATURE:
<223> OTHER INFORMATION: NLGn4 intracellular domain

<400> SEQUENCE: 8

Tyr Lys Lys Asp Lys Arg Arg His Glu Thr His Arg Arg Pro Ser Pro
1               5                   10                  15

Gln Arg Asn Thr Thr Asn Asp Ile Ala His Ile Gln Asn Glu Glu Ile
            20                  25                  30

Met Ser Leu Gln Met Lys Gln Leu Glu His Asp His Glu Cys Glu Ser
        35                  40                  45

Leu Gln Ala His Asp Thr Leu Arg Leu Thr Cys Pro Pro Asp Tyr Thr
    50                  55                  60

Leu Thr Leu Arg Arg Ser Pro Asp Asp Ile Pro Leu Met Thr Pro Asn
65                  70                  75                  80

Thr Ile Thr Met Ile Pro Asn Thr Leu Thr Gly Met Gln Pro Leu His
                85                  90                  95

Thr Phe Asn Thr Phe Ser Gly Gly Gln Asn Ser Thr Asn Leu Pro His
            100                 105                 110

Gly His Ser Thr Thr Arg Val
        115

<210> SEQ ID NO 9
<211> LENGTH: 21
<212> TYPE: PRT
<213> ORGANISM: Artificial Sequence
<220> FEATURE:
<223> OTHER INFORMATION: NLGn4 transmembrane domain

<400> SEQUENCE: 9

Val Thr Ile Ala Val Gly Ala Ser Leu Leu Phe Leu Asn Ile Leu Ala
1               5                   10                  15

Phe Ala Ala Leu Tyr
            20
```

<210> SEQ ID NO 10
<211> LENGTH: 313
<212> TYPE: PRT
<213> ORGANISM: Artificial Sequence
<220> FEATURE:
<223> OTHER INFORMATION: Nrx1b extracellular domain

<400> SEQUENCE: 10

```
Ala Ser Ser Leu Gly Ala His His Ile His His Phe His Gly Ser Ser
1               5                   10                  15

Lys His His Ser Val Pro Ile Ala Ile Tyr Arg Ser Pro Ala Ser Leu
            20                  25                  30

Arg Gly Gly His Ala Gly Thr Thr Tyr Ile Phe Ser Lys Gly Gly Gly
        35                  40                  45

Gln Ile Thr Tyr Lys Trp Pro Pro Asn Asp Arg Pro Ser Thr Arg Ala
    50                  55                  60

Asp Arg Leu Ala Ile Gly Phe Ser Thr Val Gln Lys Glu Ala Val Leu
65                  70                  75                  80

Val Arg Val Asp Ser Ser Ser Gly Leu Gly Asp Tyr Leu Glu Leu His
                85                  90                  95

Ile His Gln Gly Lys Ile Gly Val Lys Phe Asn Val Gly Thr Asp Asp
            100                 105                 110

Ile Ala Ile Glu Glu Ser Asn Ala Ile Ile Asn Asp Gly Lys Tyr His
        115                 120                 125

Val Val Arg Phe Thr Arg Ser Gly Gly Asn Ala Thr Leu Gln Val Asp
    130                 135                 140

Ser Trp Pro Val Ile Glu Arg Tyr Pro Ala Gly Arg Gln Leu Thr Ile
145                 150                 155                 160

Phe Asn Ser Gln Ala Thr Ile Ile Ile Gly Gly Lys Glu Gln Gly Gln
                165                 170                 175

Pro Phe Gln Gly Gln Leu Ser Gly Leu Tyr Tyr Asn Gly Leu Lys Val
            180                 185                 190

Leu Asn Met Ala Ala Glu Asn Asp Ala Asn Ile Ala Ile Val Gly Asn
        195                 200                 205

Val Arg Leu Val Gly Glu Val Pro Ser Ser Met Thr Thr Glu Ser Thr
    210                 215                 220

Ala Thr Ala Met Gln Ser Glu Met Ser Thr Ser Ile Met Glu Thr Thr
225                 230                 235                 240

Thr Thr Leu Ala Thr Ser Thr Ala Arg Arg Gly Lys Pro Pro Thr Lys
                245                 250                 255

Glu Pro Ile Ser Gln Thr Thr Asp Asp Ile Leu Val Ala Ser Ala Glu
            260                 265                 270

Cys Pro Ser Asp Asp Glu Asp Ile Asp Pro Cys Glu Pro Ser Ser Gly
        275                 280                 285

Gly Leu Ala Asn Pro Thr Arg Ala Gly Gly Arg Glu Pro Tyr Pro Gly
    290                 295                 300

Ser Ala Glu Val Ile Arg Glu Ser Ser
305                 310
```

<210> SEQ ID NO 11
<211> LENGTH: 56
<212> TYPE: PRT
<213> ORGANISM: Artificial Sequence
<220> FEATURE:
<223> OTHER INFORMATION: Nrx1b intracellular domain

```
<400> SEQUENCE: 11

Met Tyr Lys Tyr Arg Asn Arg Asp Glu Gly Ser Tyr His Val Asp Glu
1               5                   10                  15

Ser Arg Asn Tyr Ile Ser Asn Ser Ala Gln Ser Asn Gly Ala Val Val
                20                  25                  30

Lys Glu Lys Gln Pro Ser Ser Ala Lys Ser Ser Asn Lys Asn Lys Lys
        35                  40                  45

Asn Lys Asp Lys Glu Tyr Tyr Val
    50                  55

<210> SEQ ID NO 12
<211> LENGTH: 23
<212> TYPE: PRT
<213> ORGANISM: Artificial Sequence
<220> FEATURE:
<223> OTHER INFORMATION: Nrx1b transmembrane domain

<400> SEQUENCE: 12

Ser Thr Thr Gly Met Val Val Gly Ile Val Ala Ala Ala Ala Leu Cys
1               5                   10                  15

Ile Leu Ile Leu Leu Tyr Ala
            20

<210> SEQ ID NO 13
<211> LENGTH: 6
<212> TYPE: PRT
<213> ORGANISM: Artificial Sequence
<220> FEATURE:
<223> OTHER INFORMATION: linker peptide

<400> SEQUENCE: 13

Ile Glu Gly Arg Met Asp
1               5
```